US012559515B2

(12) United States Patent
Dhar et al.

(10) Patent No.: US 12,559,515 B2
(45) Date of Patent: Feb. 24, 2026

(54) CAP COMPOUNDS AND RNAS COMPRISING THE SAME

(71) Applicant: Helix Nanotechnologies Inc, Boston, MA (US)

(72) Inventors: Nikhil Dhar, Boston, MA (US); Nikolai Eroshenko, Boston, MA (US)

(73) Assignee: Helix Nanotechnologies Inc, Boston, MA (US)

( * ) Notice: Subject to any disclaimer, the term of this patent is extended or adjusted under 35 U.S.C. 154(b) by 0 days.

(21) Appl. No.: 18/990,530

(22) Filed: Dec. 20, 2024

(65) Prior Publication Data

US 2025/0206770 A1 Jun. 26, 2025

Related U.S. Application Data

(60) Provisional application No. 63/614,050, filed on Dec. 22, 2023.

(51) Int. Cl.
*C07H 21/02* (2006.01)
*A61K 31/7105* (2006.01)
*C12P 19/34* (2006.01)

(52) U.S. Cl.
CPC ......... *C07H 21/02* (2013.01); *A61K 31/7105* (2013.01); *C12P 19/34* (2013.01)

(58) Field of Classification Search
CPC ...... C07H 31/02; A61K 31/7105; C12P 19/34
USPC ..................... 435/6.1, 91.1, 91.31, 455, 458; 514/44 A, 44 R; 536/23.1, 24.5, 25.6
See application file for complete search history.

(56) References Cited

U.S. PATENT DOCUMENTS

2023/0331763 A1* 10/2023 Cheng ..................... C12P 19/34
2023/0383287 A1* 11/2023 Dhar .................. A61K 31/7115

FOREIGN PATENT DOCUMENTS

WO WO-2023/215516 A2 11/2023
WO WO-2025/137486 A1 6/2025

OTHER PUBLICATIONS

Burman, J. et al., Interaction of Human Complement with Sbi, a Staphylococcal Immunoglobulin-binding Protein: Indications of a Novel Mechanism of Complement Evasion by *Staphylococcus aureus*, J. Biol. Chem; 283:17579-17593 (2008).
Clark, E. et al., A structural basis for Staphylococcal complement subversion: X-ray structure of the complement-binding domain of *Staphylococcus aureus* protein Sbi in complex with ligand C3d, Mol Immunol., 48(4): 452-462 (2011).
Decroly, E. et al., Conventional and unconventional mechanisms for capping viral mRNA, Nature Reviews, 10: 51-65 (2012).
Ramanathan, A. et al., mRNA capping: biological functions and applications, Nucleic Acids Res; 44(16): 7511-7526 (2016).
International Search Report for PCT/US24/61341, 3 pages (mailed Jun. 6, 2025).
Written Opinion for PCT/US24/61341, 7 pages (mailed Jun. 6, 2025).

* cited by examiner

*Primary Examiner* — Jane J Zara
(74) *Attorney, Agent, or Firm* — Choate, Hall & Stewart LLP; Stephanie L. Schonewald; Mandeep Kaur

(57) ABSTRACT

Disclosed herein are 5' cap structures comprising a 2'-O-acetyl ribose. Also provided herein are polyribonucleotides comprising a 5' cap structure disclosed herein and compositions comprising the same as well as methods of making and using the same.

29 Claims, 3 Drawing Sheets

CAP COMPOUNDS AND RNAS COMPRISING THE SAME

CROSS REFERENCE TO RELATED APPLICATIONS

This application claims priority to and the benefit of U.S. Provisional Patent Application No. 63/614,050 filed on Dec. 22, 2023, the entire contents of which are hereby incorporated by reference in its entirety.

SEQUENCE LISTING

The instant application contains a Sequence Listing which has been submitted electronically in XML format, and is hereby incorporated by reference in its entirety. Said XML copy, created on Jan. 15, 2026, is named 2012611-0154.xml and is 4,861 bytes in size.

BACKGROUND

RNA therapeutics is a new and emerging field.

SUMMARY

Among other things, the present disclosure provides technologies for making polyribonucleotides comprising a 5' cap structure, e.g., as described herein. In some embodiments, a cap structure comprises an acyl group (e.g., a —C(═O)$CH_3$). The present disclosure is the first to demonstrate the surprising finding that polyribonucleotides comprising a cap structure comprising 2'-O-acetyl ribose can be produced at similar yields as polyribonucleotides comprising a cap structure comprising a 2'-O-methyl ribose. Accordingly, provided herein are 5' cap structures, polyribonucleotides comprising such 5' cap structures, and methods of making and using the same.

Among other things, the present disclosure provides a cap structure comprising a compound of Formula I:

I

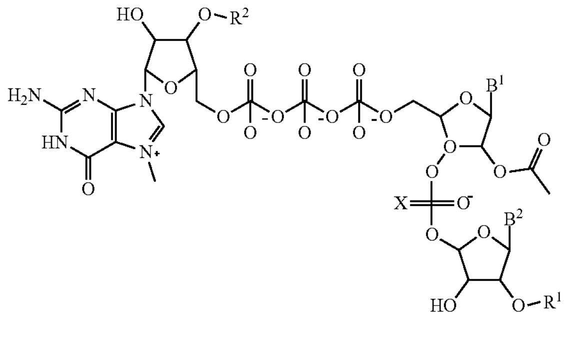

or a salt thereof, wherein:

each of $B^1$ and $B^2$ is independently selected from a natural base and a modified base;

$R^1$ is selected from hydrogen, $C_{1-6}$ alkyl, and —C(═O)$CH_3$;

$R^2$ is hydrogen or —$CH_3$; and

X is O or S.

In some embodiments, $B^1$ and $B^2$ is independently selected from a natural base and a modified base.

In some embodiments, $B^1$ is a natural base. In some embodiments, $B^1$ is adenine. In some embodiments, $B^1$ is cytosine. In some embodiments, $B^1$ is guanine. In some embodiments, $B^1$ is uracil.

In some embodiments, $B^1$ is a modified base. In some embodiments, $B^1$ is selected from N1-methylpseudouracil, a pyridin-4-one, 5-aza-uracil, 6-aza-uracil, 2-thio-5-aza-uracil, 2-thio-uracil, 5-methyl cytosine, 5-aza-cytosine, 6-aza-cytosine, pseudoisocytosine, 3-methyl-cytosine, 5-formyl-cytosine, N4-methyl-cytosine, a 2-amino-purine, a 2,6-diaminopurine, a 2-amino-6-halo-purine, a 6-halo-purine, hypoxanthine, 1-methyl-hypoxanthine, 4,6-dimethyl-3,3a,4,9a-tetrahydro-9H-imidazo[1,2-a]purin-9-one, 4,6,7-trimethyl-3,3a, 4,9a-tetrahydro-9H-imidazo[1,2-a]purin-9-one, N4-acetylcytosine, and hydroxymethyluracil.

In some embodiments, $B^2$ is a natural base. In some embodiments, $B^2$ is adenine. In some embodiments, $B^2$ is cytosine. In some embodiments, $B^2$ is guanine. In some embodiments, $B^2$ is uracil.

In some embodiments, $B^2$ is a modified base. In some embodiments, $B^2$ is selected from N1-methylpseudouracil, a pyridin-4-one, 5-aza-uracil, 6-aza-uracil, 2-thio-5-aza-uracil, 2-thio-uracil, 5-methyl cytosine, 5-aza-cytosine, 6-aza-cytosine, pseudoisocytosine, 3-methyl-cytosine, 5-formyl-cytosine, N4-methyl-cytosine, a 2-amino-purine, a 2,6-diaminopurine, a 2-amino-6-halo-purine, a 6-halo-purine, hypoxanthine, 1-methyl-hypoxanthine, 4,6-dimethyl-3,3a,4,9a-tetrahydro-9H-imidazo[1,2-a]purin-9-one, 4,6,7-trimethyl-3,3a,4,9a-tetrahydro-9H-imidazo[1,2-a]purin-9-one, N4-acetylcytosine, and 5-hydroxymethyluracil.

In some embodiments, $R^1$ is hydrogen. In some embodiments, $R^1$ is $C_{1-6}$ alkyl. In some embodiments, $R^1$ is —C(═O)$CH_3$.

In some embodiments, $R^2$ is hydrogen. In some embodiments, $R^2$ is $CH_3$.

In some embodiments, X is O. In some embodiments, X is S.

In some embodiments, a compound is selected from Formulae I-a, I-b, I-c, I-d, I-e, and I-f:

I-a

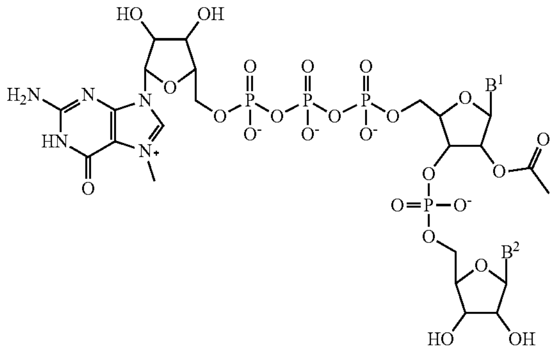

I-b

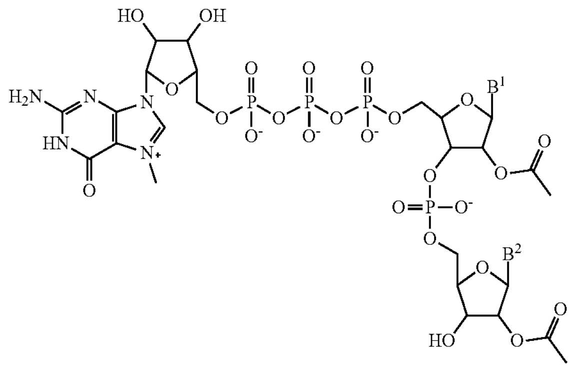

-continued

I-c

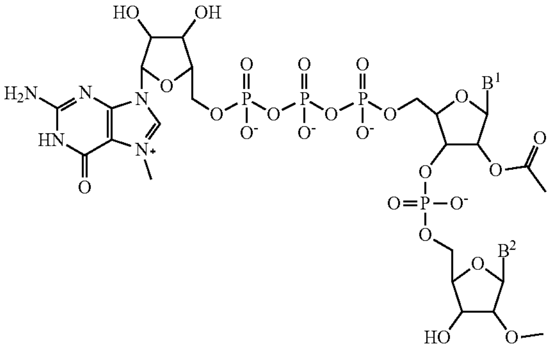

I-d

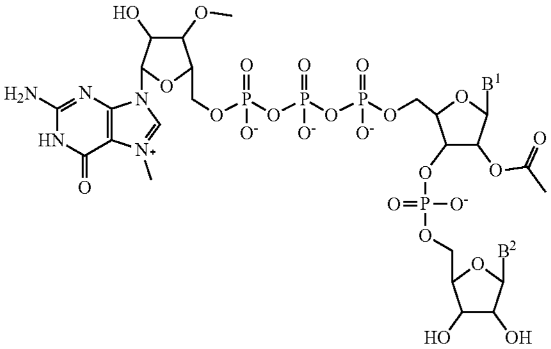

I-e

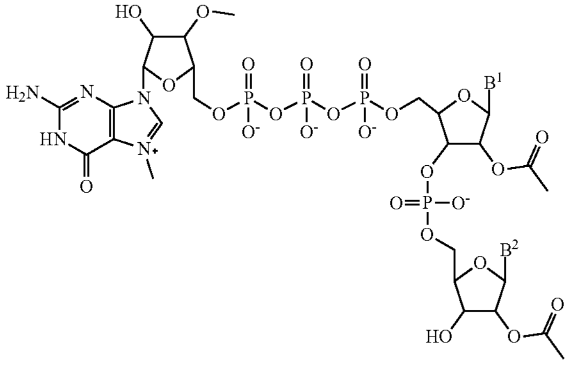

I-f

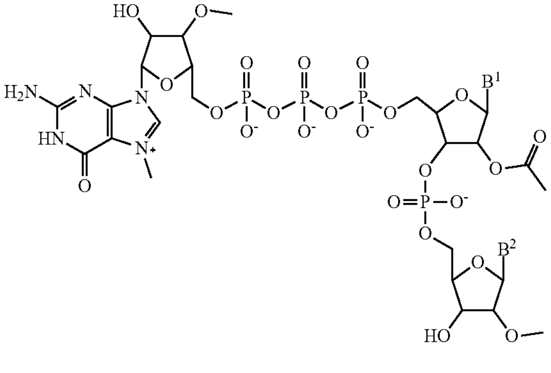

or a salt thereof.

In some embodiments, $R^1$ is hydrogen. In some embodiments, $R^1$ is $C_{1-6}$ alkyl. In some embodiments, $R^1$ is —$CH_3$. In some embodiments, $R^1$ is —C(═O)$CH_3$.

In some embodiments, $R^2$ is hydrogen. In some embodiments, $R^2$ is —$CH_3$.

In some embodiments, X is O. In some embodiments, X is S.

In some embodiments, $B^1$ and/or $B^2$ is a modified base. In some embodiments, $B^1$ and/or $B^2$ is selected from N1-methylpseudouracil, a pyridin-4-one, 5-aza-uracil, 6-aza-uracil, 2-thio-5-aza-uracil, 2-thio-uracil, 5-methyl cytosine, 5-aza-cytosine, 6-aza-cytosine, pseudoisocytosine, 3-methyl-cytosine, 5-formyl-cytosine, N4-methyl-cytosine, a 2-amino-purine, a 2,6-diaminopurine, a 2-amino-6-halo-purine, a 6-halo-purine, hypoxanthine, 1-methyl-hypoxanthine, 4,6-dimethyl-3,3a,4,9a-tetrahydro-9H-imidazo[1,2-a]purin-9-one, 4,6,7-trimethyl-3,3a,4,9a-tetrahydro-9H-imidazo[1,2-a]purin-9-one, N4-acetylcytosine, and 5-hydroxymethyluracil.

In some embodiments, $B^1$ and/or $B^2$ is a natural base. In some embodiments, $B^1$ and/or $B^2$ selected from guanine, adenine, cytosine, and uracil.

The present disclosure provides, among other things, a polyribonucleotide comprising at the 5' end a compound having the Formula II:

II

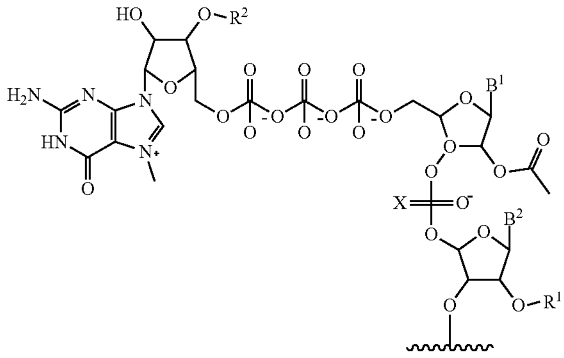

or a salt thereof, wherein:

∿∿∿ indicates the position at which the compound is attached to the polyribonucleotide;

each of $B^1$ and $B^2$ is independently selected from a natural base and a modified base;

$R^1$ is selected from hydrogen, $C_{1-6}$ alkyl, and —C(═O)$CH_3$;

$R^2$ is hydrogen or —$CH_3$; and

X is O or S.

Also provided herein, among other things, is a polyribonucleotide comprising at the 5' end a compound having a formula selected from any of Formulae II-a, II-b, II-c, II-d, II-e, and II-f:

II-a
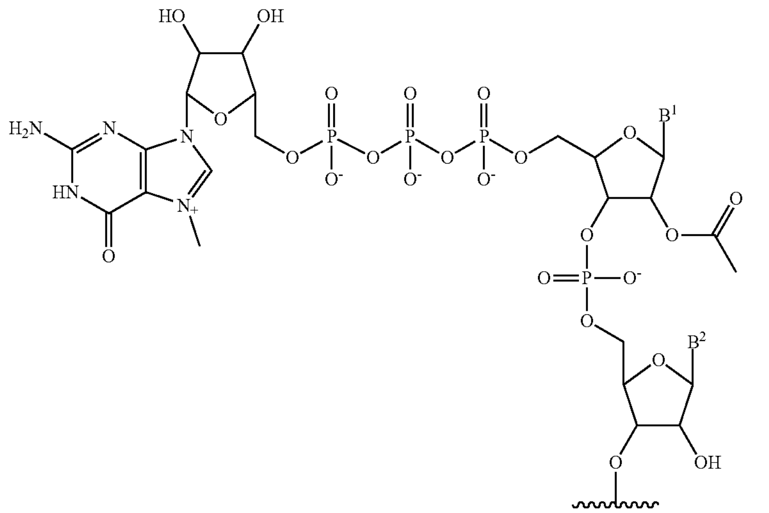
II-b
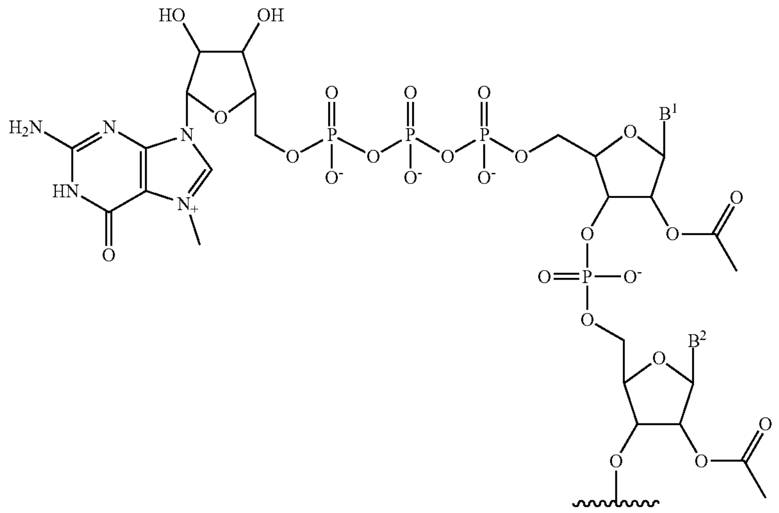
II-c
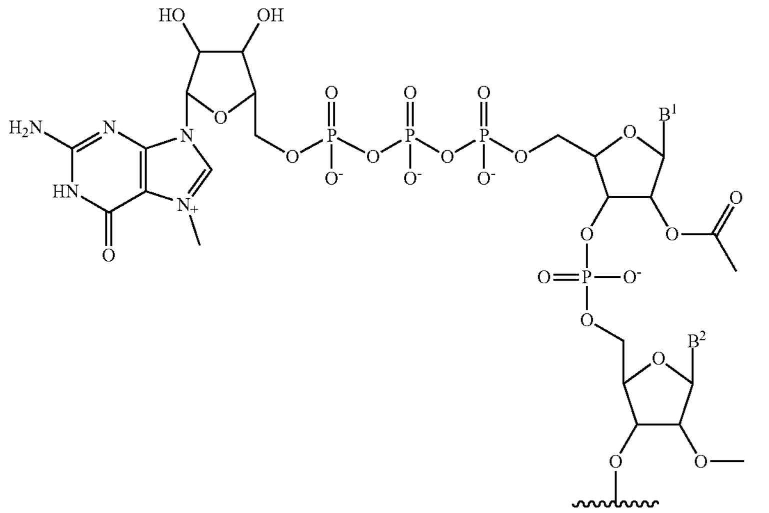

-continued
II-d
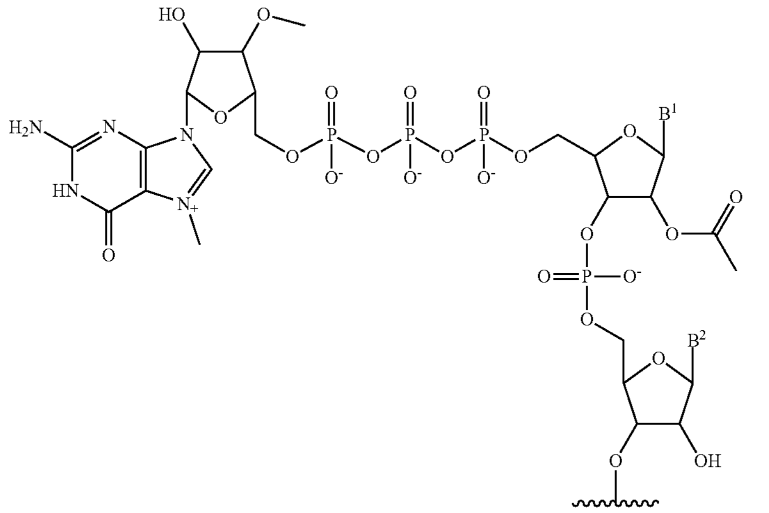
II-e
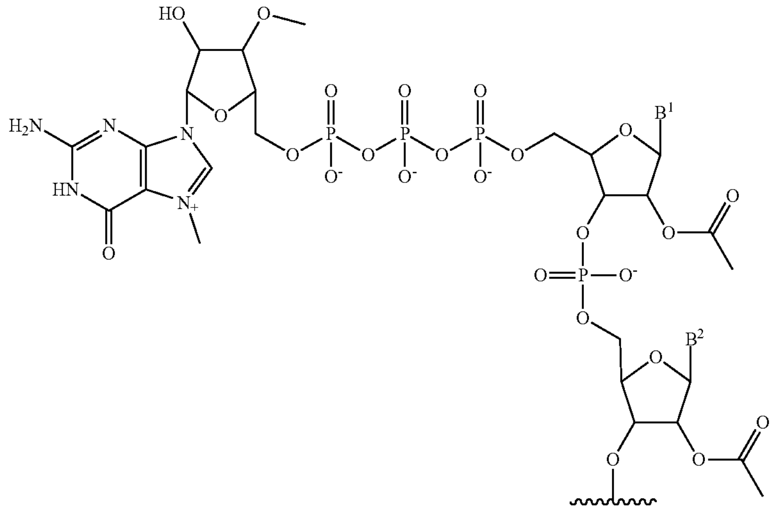
II-f
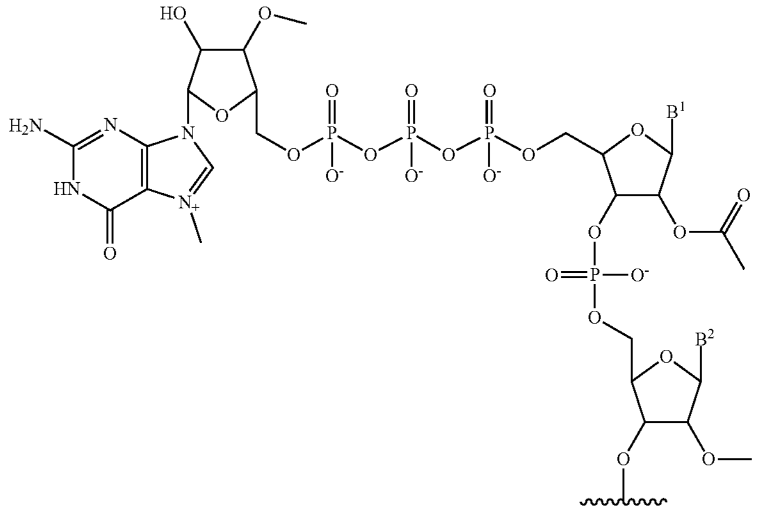
or a salt thereof.

In some embodiments, $B^1$ is a natural base. In some embodiments, $B^1$ is adenine. In some embodiments, $B^1$ is cytosine. In some embodiments, $B^1$ is guanine. In some embodiments, $B^1$ is uracil.

In some embodiments, $B^1$ is a modified base. In some embodiments, $B^1$ is selected from N1-methylpseudouracil, a pyridin-4-one, 5-aza-uracil, 6-aza-uracil, 2-thio-5-aza-uracil, 2-thio-uracil, 5-methyl cytosine, 5-aza-cytosine, 6-aza-cytosine, pseudoisocytosine, 3-methyl-cytosine, 5-formyl-cytosine, N4-methyl-cytosine, a 2-amino-purine, a 2,6-diaminopurine, a 2-amino-6-halo-purine, a 6-halo-purine, hypoxanthine, 1-methyl-hypoxanthine, 4,6-dimethyl-3,3a,4,9a-tetrahydro-9H-imidazo[1,2-a]purin-9-one, 4,6,7-trimethyl-3,3a,4,9a-tetrahydro-9H-imidazo[1,2-a]purin-9-one, N4-acetylcytosine, and 5-hydroxymethyluracil.

In some embodiments, $B^1$ comprises a modified ribose. In some embodiments, a modified ribose is a 2'-O-acetylated ribose.

In some embodiments, $B^2$ is a natural base. In some embodiments, $B^2$ is adenine. In some embodiments, $B^2$ is cytosine. In some embodiments, $B^2$ is guanine. In some embodiments, $B^2$ is uracil. In some embodiments, $B^2$ is a modified base. In some embodiments, $B^2$ is selected from N1-methylpseudouracil, a pyridin-4-one, 5-aza-uracil, 6-aza-uracil, 2-thio-5-aza-uracil, 2-thio-uracil, 5-methyl cytosine, 5-aza-cytosine, 6-aza-cytosine, pseudoisocytosine, 3-methyl-cytosine, 5-formyl-cytosine, N4-methyl-cytosine, a 2-amino-purine, a 2,6-diaminopurine, a 2-amino-6-halo-purine, a 6-halo-purine, hypoxanthine, 1-methyl-hypoxanthine, 4,6-dimethyl-3,3a,4,9a-tetrahydro-9H-imidazo[1,2-a]purin-9-one, 4,6,7-trimethyl-3,3a,4,9a-tetrahydro-9H-imidazo[1,2-a]purin-9-one, N4-acetylcytosine, and hydroxymethyluracil.

In some embodiments, $B^1$ comprises a modified ribose. In some embodiments, a modified ribose is a 2'-O-acetylated ribose.

In some embodiments, $R^1$ is hydrogen. In some embodiments, $R^1$ is $C_{1-6}$ alkyl. In some embodiments, $R^1$ is $-C(=O)CH_3$.

In some embodiments, $R^2$ is hydrogen. In some embodiments, $R^2$ is $-CH_3$.

In some embodiments, X is O. In some embodiments, X is S.

In some embodiments, a polyribonucleotide described herein further comprises one or more modified ribonucleotides comprising: a modified nucleobase, a modified ribose, a modified backbone, or any combination thereof.

In some embodiments, one or more modified ribonucleotides comprises a modified nucleobase. In some embodiments, a modified nucleobase is N4-acetylcytosine:

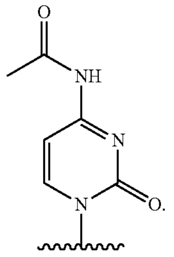 [SMILES: *n1ccc(NC(C)=O)nc1=O]

In some embodiments, a modified nucleobase is 5-hydroxymethyluracil:

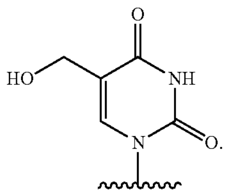 [SMILES: *n1cc(CO)c(=O)[nH]c1=O]

In some embodiments, a modified nucleobase is selected from: N1-methylpseudouracil, a pyridin-4-one, 5-aza-uracil, 6-aza-uracil, 2-thio-5-aza-uracil, 2-thio-uracil, 5-methyl cytosine, 5-aza-cytosine, 6-aza-cytosine, pseudoisocytosine, 3-methyl-cytosine, 5-formyl-cytosine, N4-methyl-cytosine, a 2-amino-purine, a 2,6-diaminopurine, a 2-amino-6-halo-purine, a 6-halo-purine, hypoxanthine, 1-methyl-hypoxanthine, 4,6-dimethyl-3,3a,4,9a-tetrahydro-9H-imidazo[1,2-a]purin-9-one, and 4,6,7-trimethyl-3,3a,4,9a-tetrahydro-9H-imidazo[1,2-a]purin-9-one. In some embodiments, a polyribonucleotide as described herein comprises a modified ribose. In some embodiments, a modified ribose comprises a 2'-O-acetyl group.

In some embodiments, a polyribonucleotide as described herein comprises one or more modified ribonucleotides. In some embodiments, one or more modified ribonucleotides comprises:

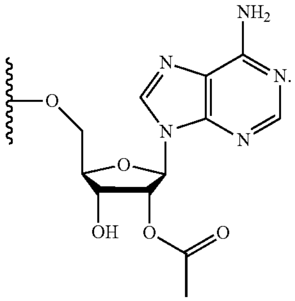

In some embodiments, one or more modified ribonucleotides comprises:

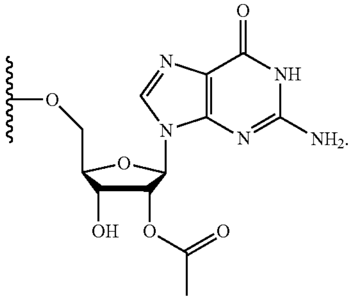

In some embodiments, one or more modified ribonucleotides comprises:

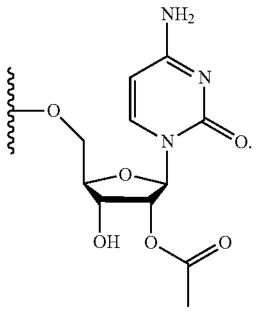

In some embodiments, one or more modified ribonucleotides comprises:

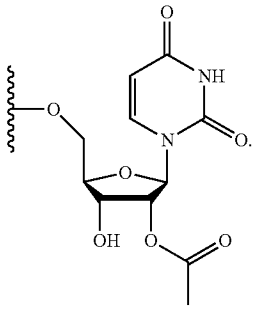

In some embodiments, one or more modified ribonucleotides comprises:

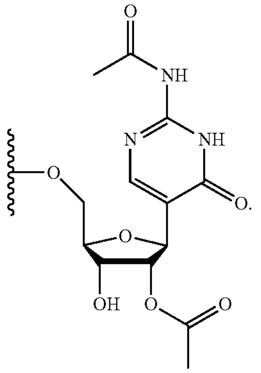

In some embodiments, one or more modified ribonucleotides comprises:

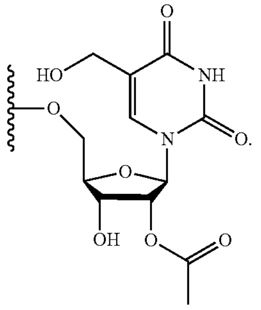

In some embodiments, one or more modified ribonucleotides comprises:

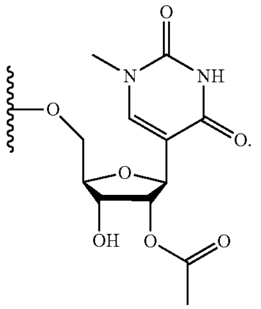

In some embodiments of any of the polyribonucleotides provided herein, a polyribonucleotide comprises a coding sequence encoding a payload. In some embodiments, a payload is or comprises a polypeptide. In some embodiments, a payload is or comprises an RNA situated in a polyribonucleotide.

The present disclosure provides, among other things, a composition comprising a polyribonucleotide as described herein. In some embodiments, a composition is a pharmaceutical composition. In some embodiments, a pharmaceutical composition is or comprises an immunogenic composition, a vaccine, a gene therapy, a chemotherapy, a protein replacement therapy, an immunotherapy, an antibody therapy, an immune-modulation therapy, a cell engineering therapy, or any combination thereof.

In some embodiments, a pharmaceutical composition is or comprises an immunogenic composition.

In some embodiments, a pharmaceutical composition is or comprises a vaccine.

In some embodiments, a pharmaceutical composition is or comprises a gene therapy.

In some embodiments, a pharmaceutical composition is or comprises a chemotherapy.

In some embodiments, a pharmaceutical composition is or comprises a protein replacement therapy.

In some embodiments, a pharmaceutical composition is or comprises an immunotherapy.

In some embodiments, a pharmaceutical composition is or comprises an antibody therapy.

In some embodiments, a pharmaceutical composition is or comprises an immune-modulation therapy.

In some embodiments, a pharmaceutical composition is or comprises a cell engineering therapy.

The present disclosure provides, among other things, a cell comprising a polyribonucleotide as described herein.

The present disclosure also provides, a method comprising administering one or more polyribonucleotides as described herein or a composition as described herein, to a cell, tissue, or subject.

In some embodiments, a method disclosed herein further comprises determining cell viability of a cell, tissue or subject, to which a polyribonucleotide or a composition comprising the same has been administered. In some embodiments, a cell, tissue or subject exhibits substantially the same cell viability as compared to a reference cell viability. In some embodiments, a reference cell viability is the viability of a cell that has been administered a polyribonucleotide that does not include a compound having the Formula II or a salt thereof; or a composition comprising a polyribonucleotide that does not include a compound having the Formula II or a salt thereof.

In some embodiments, a method described herein further comprises determining expression and/or activity of a payload. In some embodiments, a payload is or comprises a polypeptide encoded by a polyribonucleotide. In some embodiments, a payload is or comprises an RNA situated in a polyribonucleotide.

In some embodiments of a method described herein, a cell, tissue or subject described which has been administered a polyribonucleotide or a composition comprising the same exhibits substantially similar expression and/or activity of a payload as compared to expression and/or activity of a payload in a reference cell, tissue or subject.

In some embodiments of a method described herein, a cell, tissue or subject described which has been administered a polyribonucleotide or a composition comprising the same exhibits increased expression and/or activity of a payload as compared to expression and/or activity of a payload in a reference cell, tissue or subject.

In some embodiments, a reference cell, tissue or subject comprises a cell, tissue or subject that has been administered: a polyribonucleotide that does not include a compound having the Formula II or a salt thereof; or a composition comprising a polyribonucleotide that does not include a compound having the Formula II or a salt thereof.

In some embodiments of a method described herein, determining expression of a payload comprises determining expression of a polyribonucleotide, or a polypeptide, or both. In some embodiments, a method comprises determining expression of a polyribonucleotide. In some embodiments, a method comprises determining expression of a polypeptide. In some embodiments, a method comprises determining expression of a polyribonucleotide and a polypeptide.

In some embodiments, a method is a treatment method.

In some embodiments, a method is a prevention method.

In some embodiments, a method is a method to stimulate an immune response.

In some embodiments, a method is an antibody therapy method.

In some embodiments, a method is an immune-modulation method.

In some embodiments, a method is a vaccination method.

In some embodiments, a method is a gene therapy method.

In some embodiments, a method is a cell therapy engineering method.

In some embodiments a method is an immunotherapy method.

In some embodiments a method is a protein replacement therapy method.

In some embodiments a method is a chemotherapeutic method.

In some embodiments of any of the methods or uses disclosed herein, a cell is a mammalian cell.

In some embodiments of any of the methods or uses disclosed herein, a tissue is a mammalian tissue.

In some embodiments of any of the methods or uses disclosed herein, a subject is a mammal. In some embodiments, a mammal is a human.

The present disclosure provides, among other things, an in vitro transcription mixture. In some embodiments, an in vitro transcription mixture comprises (i) a DNA template, (ii) at least one RNA polymerase or a variant or a fragment thereof, (iii) a plurality of ribonucleotides, (iv) a compound having the Formula II, or a salt thereof.

In some embodiments, a plurality of ribonucleotides comprises one or more modified ribonucleotides comprising: a modified nucleobase, a modified ribose, a modified backbone, or any combination thereof. In some embodiments, a modified nucleobase comprises N1-methylpseudouracil, a pyridin-4-one, 5-aza-uracil, 6-aza-uracil, 2-thio-5-aza-uracil, 2-thio-uracil, 5-methyl cytosine, 5-aza-cytosine, 6-aza-cytosine, pseudoisocytosine, 3-methyl-cytosine, 5-formyl-cytosine, N4-methyl-cytosine, a 2-amino-purine, a 2,6-diaminopurine, a 2-amino-6-halo-purine, a 6-halo-purine, hypoxanthine, 1-methyl-hypoxanthine, 4,6-dimethyl-3,3a,4,9a-tetrahydro-9H-imidazo[1,2-a]purin-9-one, 4,6,7-trimethyl-3,3a,4,9a-tetrahydro-9H-imidazo[1,2-a]purin-9-one, N4-acetylcytosine, or 5-hydroxymethyluracil, or any combination thereof. In some embodiments, a modified nucleobase comprises a modified ribose, e.g., a 2'-O acetylated ribose. The present disclosure provides, among other things, a method of making a polyribonucleotide. In some embodiments, a method of making a polyribonucleotide comprises a step of incubating an in vitro transcription mixture as described herein.

In some embodiments, in a method of making a polyribonucleotide using an in vitro transcription mixture described herein, a compound having Formula II is added to a polyribonucleotide via co-transcriptional capping.

In some embodiments, in a method of making a polyribonucleotide using an in vitro transcription mixture described herein, a compound having any one of Formulae II-a, II-b, II-c, II-d, II-e, and II-f: is added to a polyribonucleotide via co-transcriptional capping.

In some embodiments, an in vitro mixture as described herein is incubated at a pH of about 5-8. In some embodiments, a pH is about 5, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, or about 8.0.

In some embodiments, an in vitro mixture as described herein is incubated a temperature of at least 37° C.

In some embodiments, an in vitro mixture as described herein is incubated a temperature of about 45° C. to about 55° C.

In some embodiments, a method of making a polyribonucleotide disclosed herein produces a plurality of polyribonucleotides.

In some embodiments, a plurality of polyribonucleotides produced by a method disclosed herein comprise: a modified nucleobase, a modified ribose, a modified backbone, or any combination thereof. In some embodiments, a modified nucleobase comprises N1-methylpseudouracil, a pyridin-4-one, 5-aza-uracil, 6-aza-uracil, 2-thio-5-aza-uracil, 2-thio-uracil, 5-methyl cytosine, 5-aza-cytosine, 6-aza-cytosine, pseudoisocytosine, 3-methyl-cytosine, 5-formyl-cytosine, N4-methyl-cytosine, a 2-amino-purine, a 2,6-diaminopurine, a 2-amino-6-halo-purine, a 6-halo-purine, hypoxanthine, 1-methyl-hypoxanthine, 4,6-dimethyl-3,3a,4,9a-tetrahydro-9H-imidazo[1,2-a]purin-9-one, 4,6,7-trimethyl-3,3a,4,9a-tetrahydro-9H-imidazo[1,2-a]purin-9-one, N4-acetylcytosine, or 5-hydroxymethyluracil, or any combination thereof. In some embodiments, a modified nucleobase comprises a modified ribose, e.g., a 2'-O acetylated ribose.

In some embodiments, a plurality of polyribonucleotides produced by a method disclosed herein comprise at the 5' end a compound having the Formula II:

II

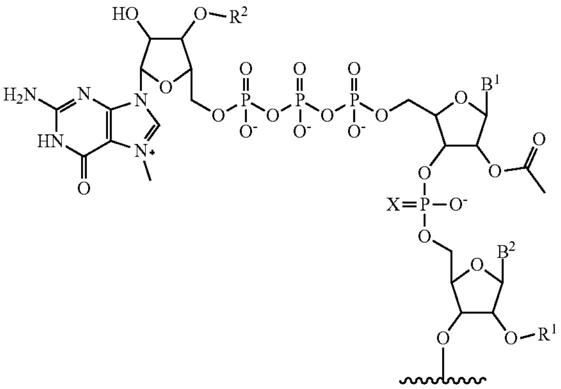

or a salt thereof, wherein:

indicates the position at which the compound is attached to the polyribonucleotide;

each of $B^1$ and $B^2$ is independently selected from a natural base and a modified base;

$R^1$ is selected from hydrogen, $C_{1-6}$ alkyl, and $-C(=O)CH_3$;

$R^2$ is hydrogen or $-CH_3$; and

X is O or S.

In some embodiments, a plurality of polyribonucleotides produced by a method disclosed herein comprise at the 5' end a formula chosen from any of Formulae II-a, II-b, II-c, II-d, II-e, and II-f:

II-a

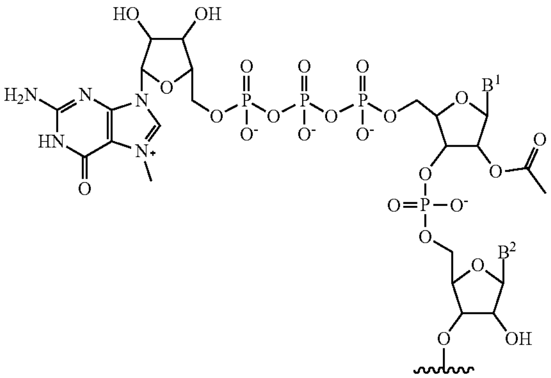

II-b

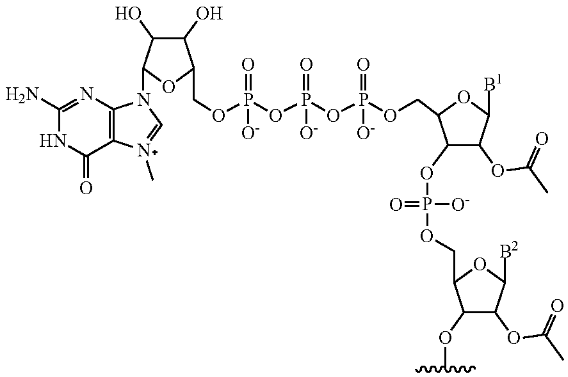

-continued

II-c

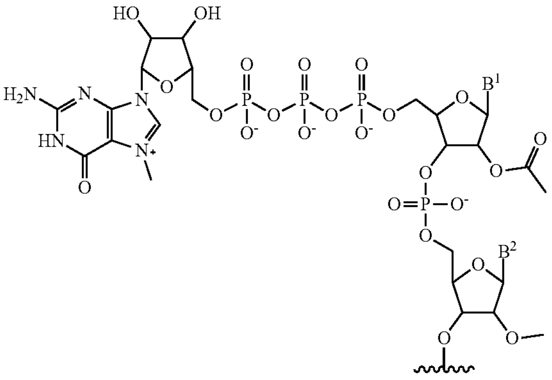

II-d

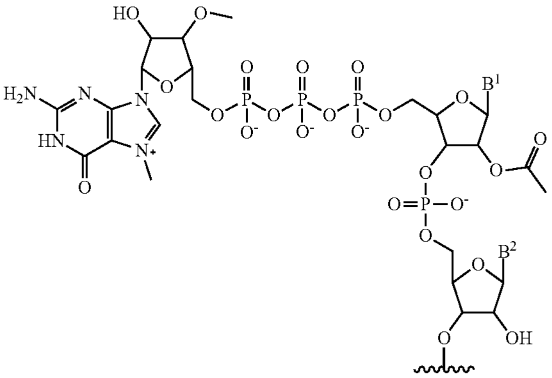

II-e

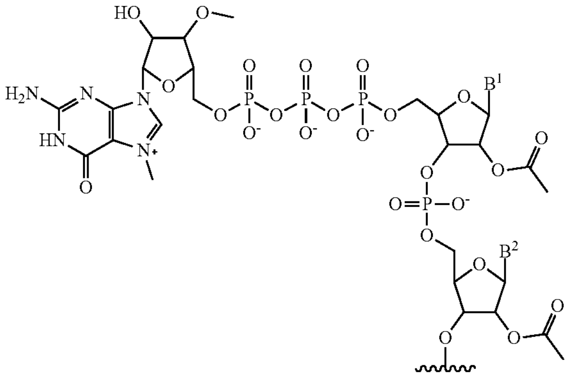

II-f

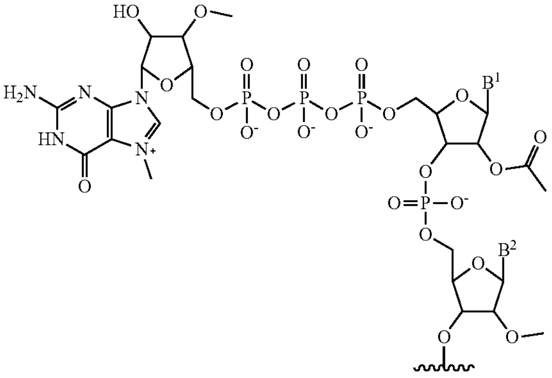

These, and other aspects encompassed by the present disclosure, are described in more detail below and in the claims.

CERTAIN DEFINITIONS

Figure 1:
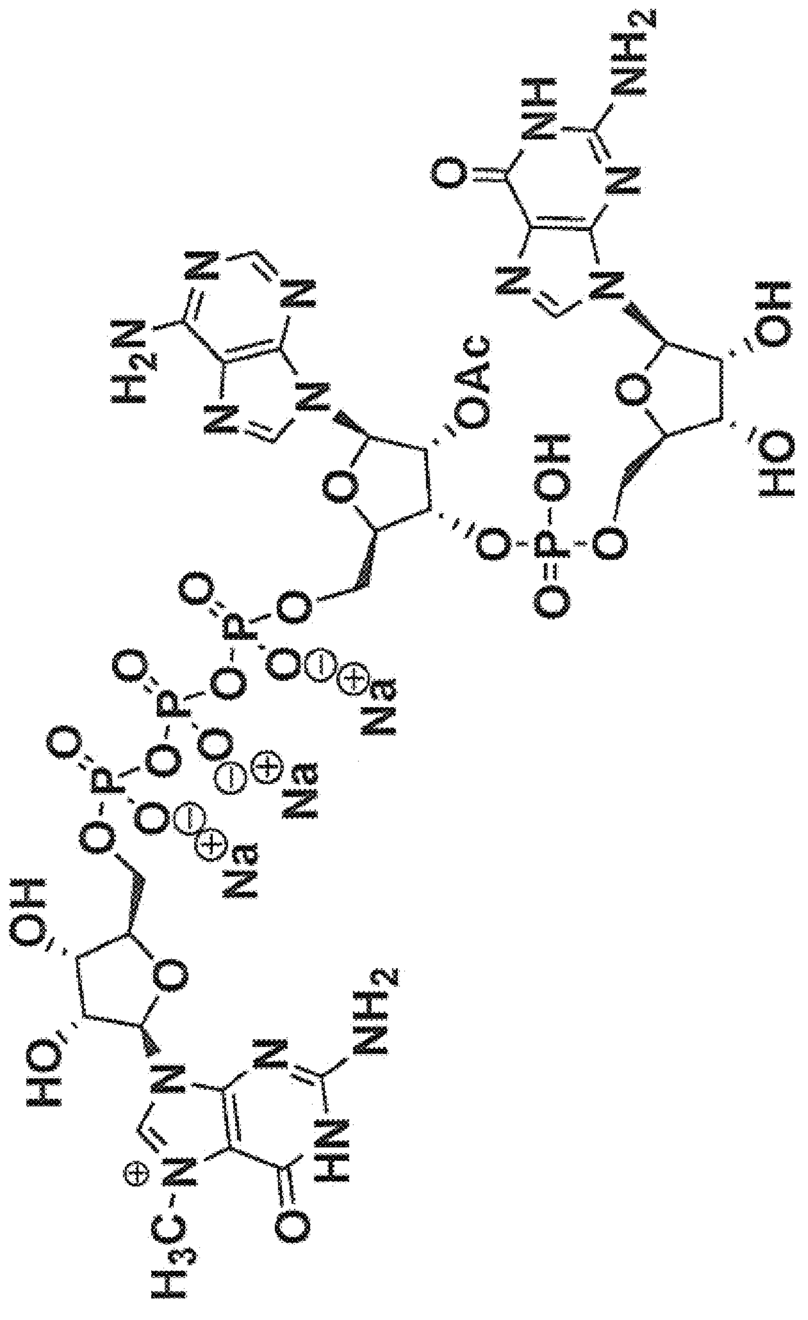
FIG. 1. is an exemplary structure of a 2'-O-acetylated cap.

Alkyl: The term “alkyl”, as used herein, means a straight-chain (i.e., unbranched) or branched, substituted or unsubstituted hydrocarbon chain that is completely saturated.

About or approximately: As used herein, the terms “about” and “approximately,” when used herein in reference to a value, refers to a value that is similar, in context to the referenced value. In general, those skilled in the art, familiar with the context, will appreciate the relevant degree of variance encompassed by “about” or “approximately” in that context. For example, in some embodiments, the term “about” or “approximately” may encompass a range of values that within 25%, 20%, 19%, 18%, 17%, 16%, 15%, 14%, 13%, 12%, 11%, 10%, 9%, 8%, 7%, 6%, 5%, 4%, 3%, 2%, 1%, or less of the referred value.

Administering: As used herein, the term “administering” or “administration” typically refers to administration of a composition to a subject to achieve delivery of an agent that is, or is included in, the composition. Those of ordinary skill in the art will be aware of a variety of routes that may, in appropriate circumstances, be utilized for administration to a subject, for example a human. For example, in some embodiments, administration may be ocular, oral, parenteral, topical, etc. In some particular embodiments, administration may be bronchial (e.g., by bronchial instillation), buccal, dermal (which may be or comprise, for example, one or more of topical to the dermis, intradermal, interdermal, transdermal, etc.), enteral, intra-arterial, intradermal, intragastric, intramedullary, intramuscular, intranasal, intraperitoneal, intrathecal, intravenous, intraventricular, within a specific organ (e.g., intrahepatic), mucosal, nasal, oral, rectal, subcutaneous, sublingual, topical, tracheal (e.g., by intratracheal instillation), vaginal, vitreal, etc. In some embodiments, administration may involve only a single dose. In some embodiments, administration may involve application of a fixed number of doses. In some embodiments, administration may involve dosing that is intermittent (e.g., a plurality of doses separated in time) and/or periodic (e.g., individual doses separated by a common period of time) dosing. In some embodiments, administration may involve continuous dosing (e.g., perfusion) for at least a selected period of time.

Antigen: The term “antigen”, as used herein, refers to an agent that elicits an immune response; and/or (ii) an agent that binds to a T cell receptor (e.g., when presented by an MHC molecule) or to an antibody. In some embodiments, an antigen elicits a humoral response (e.g., including production of antigen-specific antibodies); in some embodiments, an antigen elicits a cellular response (e.g., involving T-cells whose receptors specifically interact with the antigen). In some embodiments, an antigen comprises at least one epitope of a target protein. In some embodiments, an epitope may be a linear epitope. In some embodiments, an epitope may be a conformational epitope. In some embodiments, an antigen binds to an antibody and may or may not induce a particular physiological response in an organism. In general, an antigen may be or include any chemical entity such as, for example, a small molecule, a nucleic acid, a polypeptide, a carbohydrate, a lipid, a polymer (in some embodiments other than a biologic polymer [e.g., other than a nucleic acid or amino acid polymer]) etc. In some embodiments, an antigen is or comprises a polypeptide. In some embodiments, an antigen is or comprises a glycan. Those of ordinary skill in the art will appreciate that, in general, an antigen may be provided in isolated or pure form, or alternatively may be provided in crude form (e.g., together with other materials, for example in an extract such as a cellular extract or other relatively crude preparation of an antigen-containing source). In some embodiments, antigens utilized in accordance with the present invention are provided in a crude form. In some embodiments, an antigen is a recombinant antigen. In some embodiments, an antigen comprises a wild-type or variant sequence (e.g., an antigen variant). In some embodiments, an antigen comprises a full-length version of the antigen or a portion of the antigen (e.g. an antigen fragment or an antigen fragment variant).

Comparable: As used herein, the term “comparable” refers to two or more agents (e.g., entities or set(s) of conditions), situations, etc., that may not be identical to one another but that are sufficiently similar to permit comparison therebetween so that one skilled in the art will appreciate that conclusions may reasonably be drawn based on differences or similarities observed. In some embodiments, comparable sets of conditions, circumstances, individuals, or populations are characterized by a plurality of substantially identical features and one or a small number of varied features. Those of ordinary skill in the art will understand, in context, what degree of identity is required in any given circumstance for two or more such agents, entities, situations, sets of conditions, etc to be considered comparable. For example, those of ordinary skill in the art will appreciate that sets of circumstances, individuals, or populations are comparable to one another when characterized by a sufficient number and type of substantially identical features to warrant a reasonable conclusion that differences in results obtained or phenomena observed under or with different sets of circumstances, individuals, or populations are caused by or indicative of the variation in those features that are varied.

Delivery contacting: As used interchangeably herein, the term “delivery,” “delivering,” or “contacting” refers to introduction of a polynucleotide (e.g., as described herein) or a fusion polypeptide (e.g., as described herein) into a target cell. A target cell can be cultured in vitro or ex vivo or be present in a subject (in vivo). Methods of introducing a polynucleotide (e.g., as described herein) or a fusion polypeptide (e.g., as described herein) into a target cell can vary with in vitro, ex vivo, or in vivo applications. In some embodiments, a polynucleotide (e.g., as described herein) or a fusion polypeptide (e.g., as described herein) can be introduced into a target cell in a cell culture by in vitro transfection. In some embodiments, a polynucleotide (e.g., as described herein) or a fusion polypeptide (e.g., as described herein) can be introduced into a target cell via delivery vehicles (e.g., nanoparticles, liposomes, and/or complexation with a cell-penetrating agent). In some embodiments, a polynucleotide (e.g., as described herein) or a fusion polypeptide (e.g., as described herein) can be introduced into a target cell in a subject by administering a polynucleotide (e.g., as described herein) or a fusion polypeptide (e.g., as described herein) to a subject.

Encode: As used herein, the team "encode" or "encoding" refers to a first molecule that is produced by a second molecule, wherein the sequence information of the second molecule determines the sequence of the first molecule. For example, a first molecule can have a defined sequence of nucleotides (e.g., a polyribonucleotide) or a defined sequence of amino acids which are determined by the sequence of the second molecule (e.g., a polynucleotide). For example, a DNA molecule (e.g., a second molecule) can encode an RNA molecule (e.g., a first molecule, for example by a transcription process that includes a DNA-dependent RNA polymerase enzyme) or a polypeptide (e.g., a first molecule for example by a transcription and a translation process). An RNA molecule (e.g., a second molecule) can encode a polypeptide (e.g., a first molecule for example by a translation process). Thus, a gene, a cDNA, or an RNA molecule encodes a polypeptide if transcription and translation of RNA corresponding to that gene produces the polypeptide in a cell or other biological system.

Functional: As used herein, the term "functional" is used to refer to a form or fragment of an entity that exhibits a particular property and/or activity.

Fragment: A "fragment" of a material or entity as described herein has a structure that includes a discrete portion of the whole, but lacks one or more moieties found in the whole. In some embodiments, a fragment consists of such a discrete portion. In some embodiments, a fragment consists of or comprises a characteristic structural element or moiety found in the whole. In some embodiments, a fragment comprises a polynucleotide fragment. In some embodiments, a fragment comprises a polypeptide fragment. In some embodiments, a polynucleotide fragment or a polypeptide fragment comprises or consists of at least 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 275, 300, 325, 350, 375, 400, 425, 450, 475, 500 or more monomeric units (e.g., residues) as found in the whole polynucleotide or whole polypeptide. In some embodiments, a polynucleotide fragment or a polypeptide fragment comprises or consists of at least about 5%, 10%, 15%, 20%, 25%, 30%, 25%, 40%, 45%, 50%, 55%, 60%, 65%, 70%, 75%, 80%, 85%, 90%, 95%, 96%, 97%, 98%, 99% or more of the monomeric units (e.g., residues) found in the whole polynucleotide or whole polypeptide. The whole polypeptide or whole polynucleotide may in some embodiments be referred to as the "parent" of the polynucleotide fragment or polypeptide fragment.

Nucleic acid Oligonucleotide Polynucleotide: As used herein, the terms "nucleic acid" and "polynucleotide" and "oligonucleotide" are used interchangeably, and refer to a polymer of 3 nucleotides or more. In some embodiments, a nucleic acid comprises DNA. In some embodiments, a nucleic acid comprises RNA. In some embodiments, a nucleic acid comprises messenger RNA (mRNA). In some embodiments, a nucleic acid is single stranded. In some embodiments, a nucleic acid is double stranded. In some embodiments, a nucleic acid comprises both single and double stranded portions. In some embodiments, a nucleic acid comprises a backbone that comprises one or more phosphodiester linkages. In some embodiments, a nucleic acid comprises a backbone that comprises both phosphodiester and non-phosphodiester linkages. For example, in some embodiments, a nucleic acid may comprise a backbone that comprises one or more phosphorothioate or 5'-N-phosphoramidite linkages and/or one or more peptide bonds, e.g., as in a "peptide nucleic acid". In some embodiments, a nucleic acid comprises one or more, or all, natural residues (e.g., adenine, cytosine, deoxyadenosine, deoxycytidine, deoxyguanosine, deoxythymidine, guanine, thymine, uracil). In some embodiments, a nucleic acid comprises on or more, or all, non-natural residues. In some embodiments, a non-natural residue comprises a nucleoside analog (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, 6-O-methylguanine, 2-thiocytidine, methylated bases, intercalated bases, and combinations thereof). In some embodiments, a non-natural residue comprises one or more modified sugars (e.g., 2'-fluororibose, ribose, 2'-deoxyribose, arabinose, and hexose) as compared to those in natural residues. In some embodiments, a nucleic acid has a nucleotide sequence that encodes a functional gene product such as an RNA or polypeptide. In some embodiments, a nucleic acid has a nucleotide sequence that comprises one or more introns. In some embodiments, a nucleic acid may be prepared by isolation from a natural source, enzymatic synthesis (e.g., by polymerization based on a complementary template, e.g., in vivo or in vitro, reproduction in a recombinant cell or system, or chemical synthesis. In some embodiments, a nucleic acid is at least 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 20, 225, 250, 275, 300, 325, 350, 375, 400, 425, 450, 475, 500, 600, 700, 800, 900, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, or 20,000 or more residues or nucleotides long. When a number of nucleotides is used as an indication of size, e.g., of a polynucleotide, a certain number of nucleotides refers to the number of nucleotides on a single strand, e.g., of a polynucleotide.

Polypeptide: The term "polypeptide", as used herein, generally has its art-recognized meaning of a polymer of at least three amino acids or more. Those of ordinary skill in the art will appreciate that the term "polypeptide" is intended to be sufficiently general as to encompass not only polypeptides having a complete sequence recited herein, but also to encompass polypeptides that represent functional, biologically active, or characteristic fragments, portions or domains (e.g., fragments, portions, or domains retaining at least one activity) of such complete polypeptides. Polypeptides may contain L-amino acids, D-amino acids, or both and may contain any of a variety of amino acid modifications or analogs known in the art. Useful modifications include, e.g., terminal acetylation, amidation, methylation, etc. In some embodiments, polypeptides may comprise natural amino acids, non-natural amino acids, synthetic amino acids, and combinations thereof.

RNA oligonucleotide: As used herein, the term "RNA oligonucleotide" refers to an oligonucleotide of ribonucleotides. In some embodiments, an RNA oligonucleotide is single stranded. In some embodiments, an RNA oligonucleotide is double stranded. In some embodiments, an RNA oligonucleotide comprises both single and double stranded portions. In some embodiments, an RNA oligonucleotide can comprise a backbone structure as described in the definition of "Nucleic acid Oligonucleotide" above. An RNA oligonucleotide can be a regulatory RNA (e.g., siRNA, microRNA, etc.), or a messenger RNA (mRNA) oligonucleotide. In some embodiments an RNA oligonucleotide can comprise at its 3' end a poly(A) region. In some embodiments an RNA oligonucleotide comprises at its 5' end a cap structure, e.g., for recognizing and attachment of an RNA to a ribosome to initiate translation. In some embodiments, a polynucleotide comprises an RNA oligonucleotide. When a number of ribonucleotides is used as an indication of size, e.g., of a polynucleotide, a certain number of nucleotides refers to the number of ribonucleotides on a single strand.

Subject: As used herein, the term "subject" refers an organism, typically a mammal (e.g., a human). In some embodiments, a subject is suffering from a disease, disorder or condition. In some embodiments, a subject is susceptible to a disease, disorder, or condition. In some embodiments, a subject displays one or more symptoms or characteristics of a disease, disorder or condition. In some embodiments, a subject does not display any symptom or characteristic of a disease, disorder, or condition. In some embodiments, a subject is someone with one or more features characteristic of susceptibility to or risk of a disease, disorder, or condition. In some embodiments, a subject is a patient. In some embodiments, a subject is an individual to whom diagnosis and/or therapy is and/or has been administered.

Variant: As used herein, the term "variant" refers to an entity that shows significant structural identity with a reference entity but differs structurally from the reference entity in the presence or level of one or more chemical moieties as compared with the reference entity. In many embodiments, a variant also differs functionally from its reference entity. In general, whether a particular entity is properly considered to be a "variant" of a reference entity is based on its degree of structural identity with the reference entity. For example, a variant polypeptide may differ from a reference polypeptide as a result of one or more differences in amino acid sequence and/or one or more differences in chemical moieties (e.g., carbohydrates, lipids, etc.) covalently attached to the polypeptide backbone. Alternatively or additionally, in some embodiments, a variant polypeptide does not share at least one characteristic sequence element with a reference polypeptide. In some embodiments, the reference polypeptide has one or more biological activities. In some embodiments, a variant polypeptide shares one or more of the biological activities of the reference polypeptide. In some embodiments, a variant polypeptide lacks one or more of the biological activities of the reference polypeptide. In some embodiments, a variant polypeptide shows a reduced level of one or more biological activities as compared with the reference polypeptide.

Standard techniques may be used for recombinant DNA, oligonucleotide synthesis, e.g., RNA synthesis, and tissue culture and transformation (e.g., electroporation, lipofection). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Green and Sambrook, Molecular Cloning: A Laboratory Manual (4th ed., Cold Spring Harbor Laboratory Press, Cold Spring Harbor, N.Y. (2012)), which is incorporated herein by reference for any purpose.

DETAILED DESCRIPTION OF CERTAIN EMBODIMENTS

5' Cap

RNA capping is well researched and is described, e.g., in Decroly E et al. (2012) *Nature Reviews* 10:51-65; and in Ramanathan A. et al., (2016) *Nucleic Acids Res;* 44 (16): 7511-7526, the entire contents of each of which is hereby incorporated by reference. 5' caps include a Cap-0 (also referred herein as "Cap0"), a Cap-1 (also referred herein as "Cap1"), or Cap-2 (also referred herein as "Cap2"). See, e.g., FIG. 1 of Ramanathan A et al., and FIG. 1 of Decroly E et al.

The term "5'-cap" as used herein refers to a structure found on the 5'-end of an RNA, e.g., mRNA, and generally includes a guanosine nucleotide connected to an RNA, e.g., mRNA, via a 5'- to 5'-triphosphate linkage (also referred to as Gppp or G(5') ppp(5')).

In some embodiments, the present disclosure provides a polyribonucleotide, wherein the 5' end of the polyribonucleotide comprises a compound of Formula II:

II

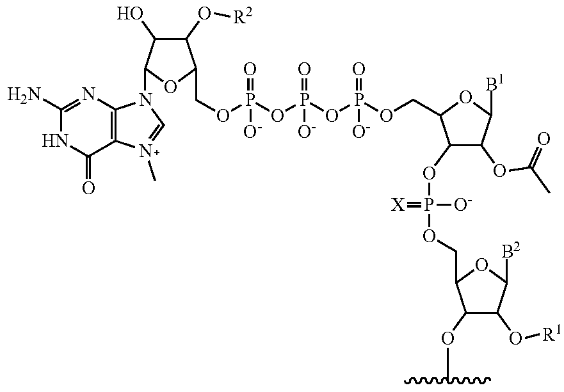

or a salt thereof, wherein:

∿∿∿ indicates the position at which the compound is attached to the polyribonucleotide;

each of $B^1$ and $B^2$ is independently selected from a natural base and a modified base;

$R^1$ is selected from hydrogen, $C_{1-6}$ alkyl, and —C(═O)$CH_3$;

$R^2$ is hydrogen or —$CH_3$; and

X is O or S.

In some embodiments, the present disclosure provides a compound of Formula I:

I

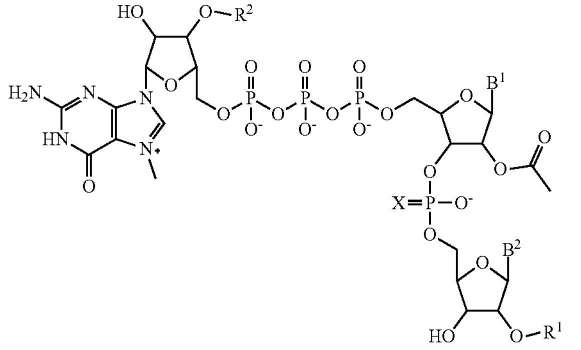

or a salt thereof, wherein:

each of $B^1$ and $B^2$ is independently selected from a natural base and a modified base;

$R^1$ is selected from hydrogen, $C_{1-6}$ alkyl, and —C(=O)$CH_3$;

$R^2$ is hydrogen or —$CH_3$; and

X is O or S.

As defined generally above for Formula I and Formula II, each of $B^1$ and $B^2$ is independently selected from a natural base and a modified base. In some embodiments, $B^1$ is a natural base. In some embodiments, $B^1$ is adenine. In some embodiments, $B^1$ is cytosine. In some embodiments, $B^1$ is guanine. In some embodiments, $B^1$ is uracil.

In some embodiments, $B^1$ is a modified base. In some embodiments, $B^1$ is selected from N1-methylpseudouracil, a pyridin-4-one, 5-aza-uracil, 6-aza-uracil, 2-thio-5-aza-uracil, 2-thio-uracil, 5-methyl cytosine, 5-aza-cytosine, 6-aza-cytosine, pseudoisocytosine, 3-methyl-cytosine, 5-formyl-cytosine, N4-methyl-cytosine, a 2-amino-purine, a 2,6-diaminopurine, a 2-amino-6-halo-purine, a 6-halo-purine, hypoxanthine, 1-methyl-hypoxanthine, 4,6-dimethyl-3,3a,4,9a-tetrahydro-9H-imidazo[1,2-a]purin-9-one, 4,6,7-trimethyl-3,3a,4,9a-tetrahydro-9H-imidazo[1,2-a]purin-9-one, N4-acetylcytosine, and 5-hydroxymethyluracil.

In some embodiments, $B^2$ is a natural base. In some embodiments, $B^2$ is adenine. In some embodiments, $B^2$ is cytosine. In some embodiments, $B^2$ is guanine. In some embodiments, $B^2$ is uracil.

In some embodiments, $B^2$ is a modified base. In some embodiments, $B^2$ is selected from N1-methylpseudouracil, a pyridin-4-one, 5-aza-uracil, 6-aza-uracil, 2-thio-5-aza-uracil, 2-thio-uracil, 5-methyl cytosine, 5-aza-cytosine, 6-aza-cytosine, pseudoisocytosine, 3-methyl-cytosine, 5-formyl-cytosine, N4-methyl-cytosine, a 2-amino-purine, a 2,6-diaminopurine, a 2-amino-6-halo-purine, a 6-halo-purine, hypoxanthine, 1-methyl-hypoxanthine, 4,6-dimethyl-3,3a,4,9a-tetrahydro-9H-imidazo[1,2-a]purin-9-one, 4,6,7-trimethyl-3,3a,4,9a-tetrahydro-9H-imidazo[1,2-a]purin-9-one, N4-acetylcytosine, and 5-hydroxymethyluracil.

As defined generally above for Formula I and Formula II, $R^1$ is selected from hydrogen, $C_{1-6}$ alkyl, and —C(=O)$CH_3$. In some embodiments, $R^1$ is hydrogen. In some embodiments, $R^1$ is $C_{1-6}$ alkyl. In some embodiments, $R^1$ is —$CH_3$. In some embodiments, $R^1$ is —C(=O)$CH_3$.

As defined generally above for Formula I and Formula II, $R^2$ is hydrogen or —$CH_3$. In some embodiments, $R^2$ is hydrogen. In some embodiments, $R^2$ is —$CH_3$.

As defined generally above for Formula I and Formula II, X is O or S. In some embodiments, X is O. In some embodiments, X is S.

In some embodiments, the present disclosure provides a compound of any of Formulae I-a, I-b, I-c, I-d, I-e, and I-f:

I-a

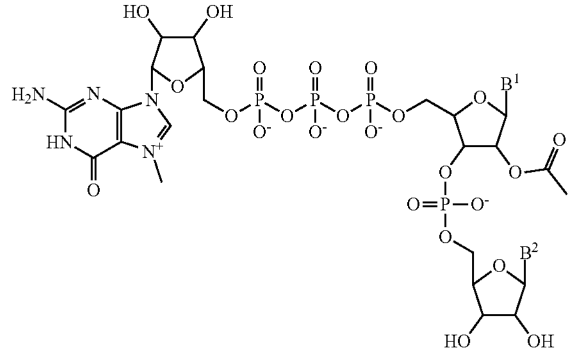

I-b

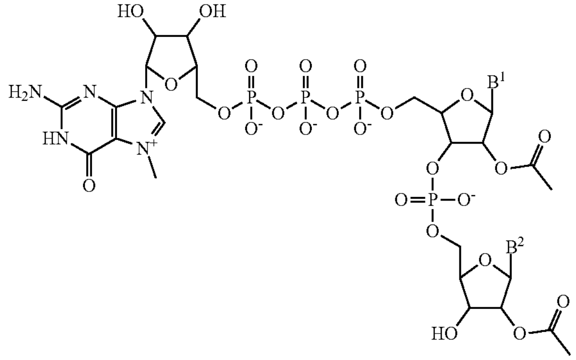

I-c

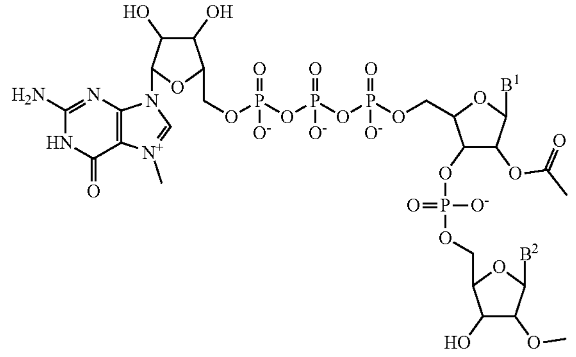

I-d

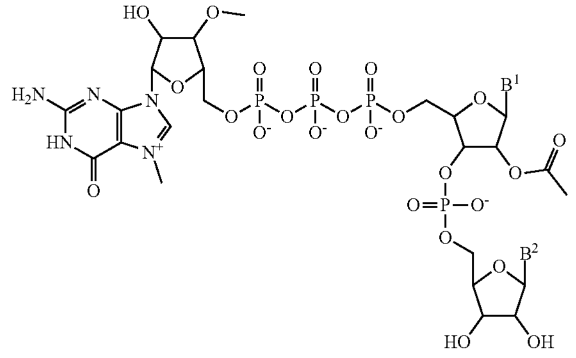

-continued
I-e
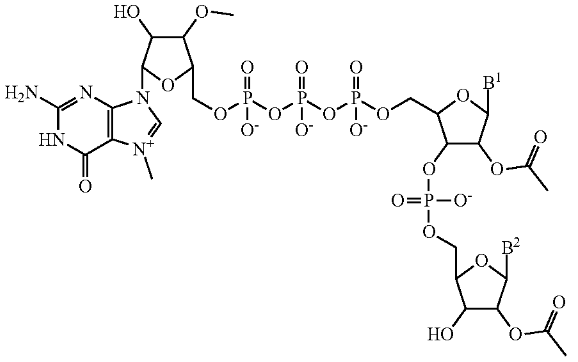
I-f
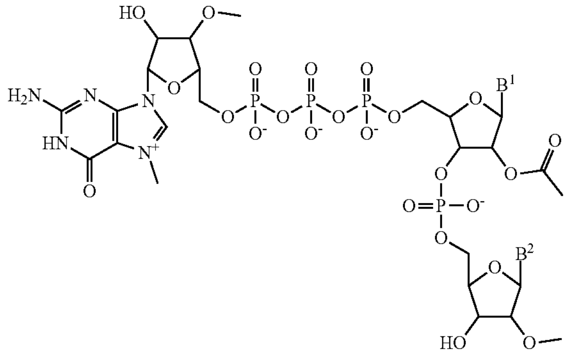
or a salt thereof, wherein each of $B^1$ and $B^2$ is as defined above and described herein.
In some embodiments, the present disclosure provides a compound of any of Formulae II-a, II-b, II-c, II-d, II-e, and II-f:
II-a
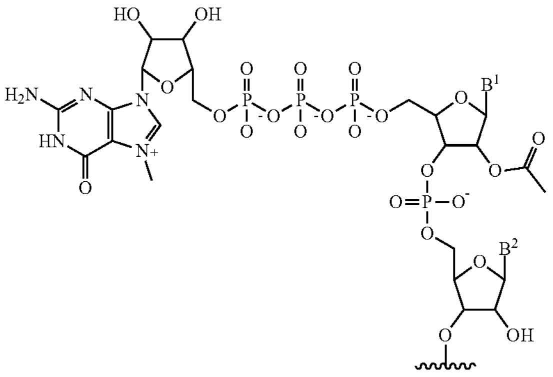
-continued
II-b
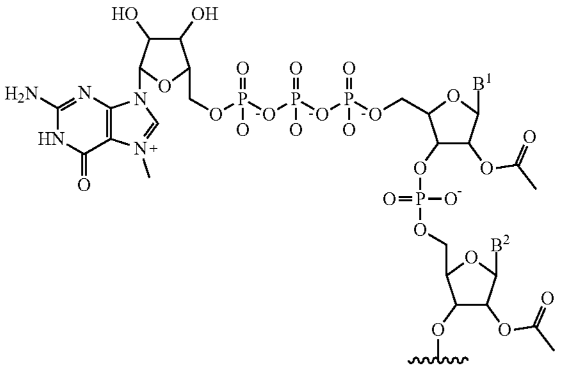
II-c
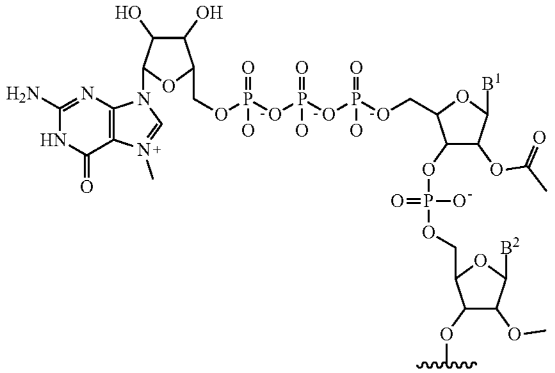
II-d
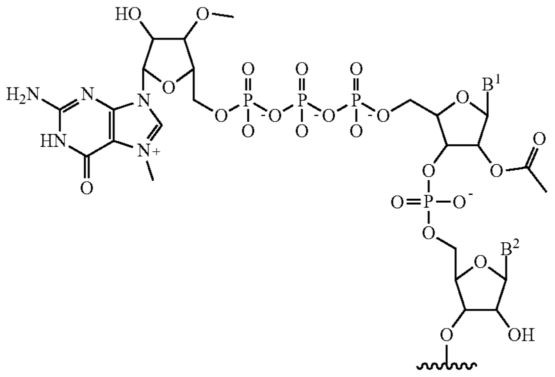
II-e
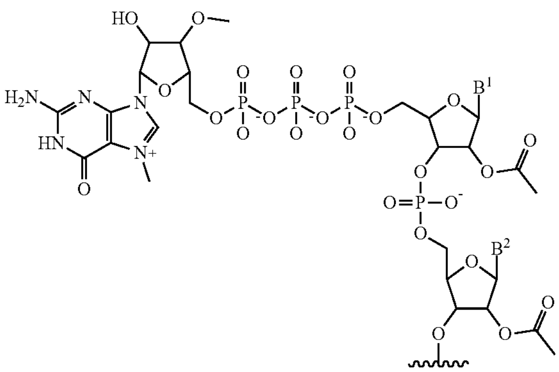

-continued
II-f
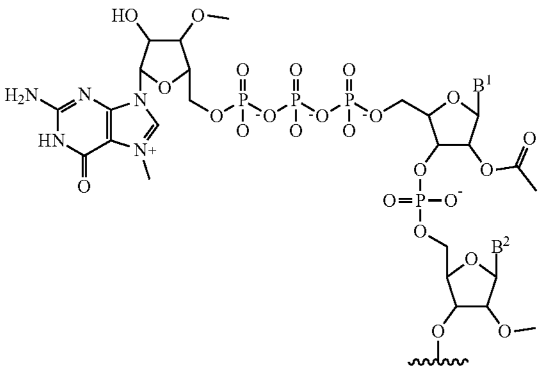
or a salt thereof, wherein each of $B^1$ and $B^2$ is as defined above and described herein.
In some embodiments, a compound of Formula I is selected from
I-1
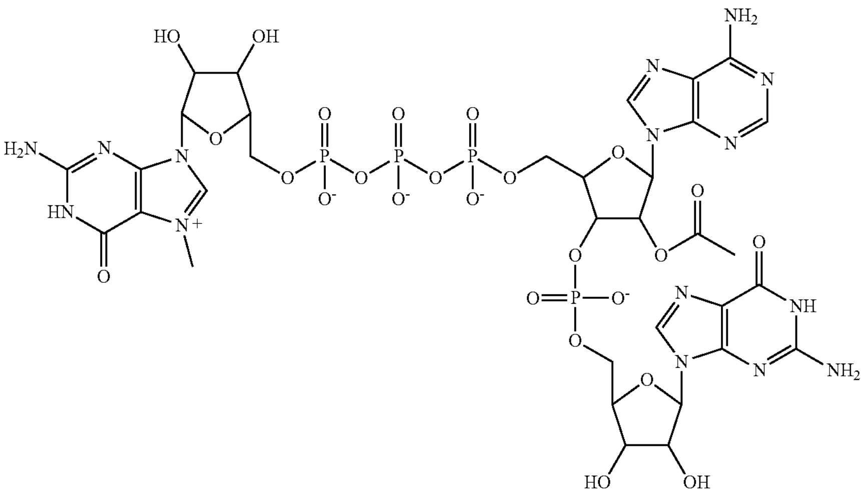
I-2
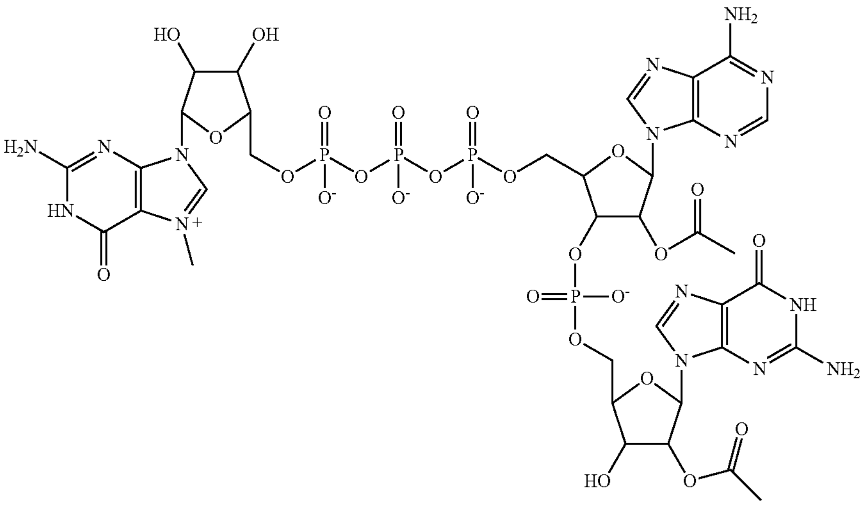
or a salt thereof.

In some embodiments, a compound of Formula II is selected from

II-1

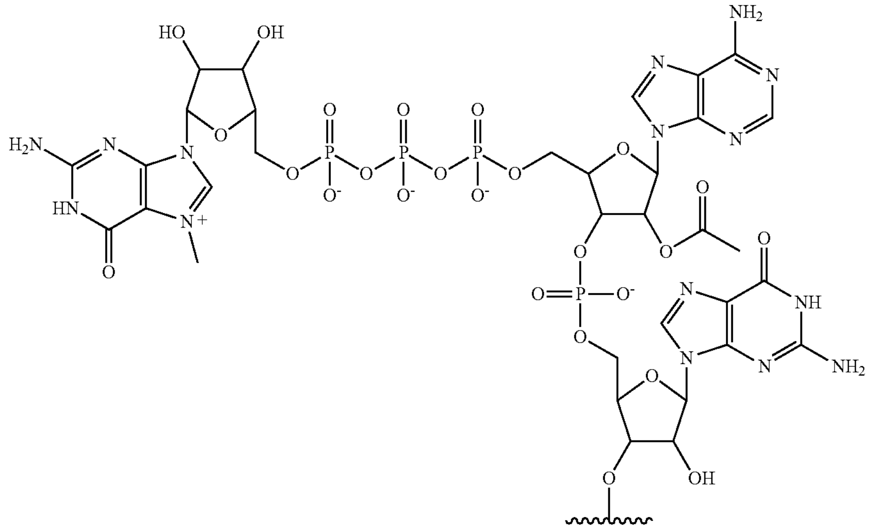

II-2

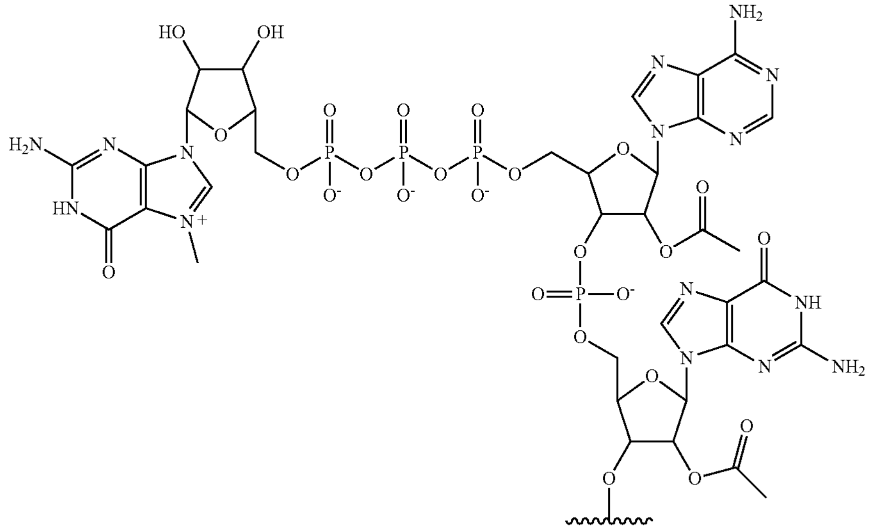

or a salt thereof.

Modified Nucleobases and Modified Ribonucleotides in Polyribonucleotides Disclosed Herein Polynucleotides disclosed herein can be a polyribonucleotide which further comprises one or more modified ribonucleotides comprising: a modified nucleobase, a modified ribose, a modified backbone, or any combination thereof.

In some embodiments, a polynucleotide is a polyribonucleotide. In some embodiments, a polyribonucleotide comprises one or more modified ribonucleotides. In some embodiments, a polyribonucleotide comprises a modified nucleobase, a modified ribose, a modified backbone, or any combination thereof.

In some embodiments, a polyribonucleotide comprises a modified nucleobase.

In some embodiments, one or more modified ribonucleotides comprises a modified nucleobase having the structure:

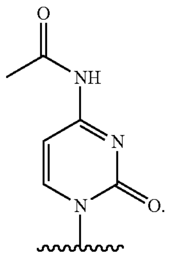 [SMILES: *n1ccc(NC(C)=O)nc1=O]

In some embodiments, a polyribonucleotide comprises cytidine residues. In some embodiments, at least 5% of cytidine residues in the polyribonucleotide are N4-acetylcytidine. In some embodiments, less than 100% of cytidine residues in the polyribonucleotide are N4-acetylcytidine. In some embodiments, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 99% of cytidine residues in the polyribonucleotide are N4-acetylcytidine.

In some embodiments, one or more modified ribonucleotides comprises a modified nucleobase having the structure:

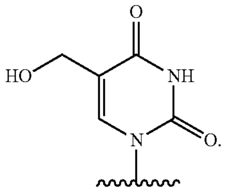 [SMILES: *n1cc(CO)c(=O)[nH]c1=O]

In some embodiments, a polyribonucleotide comprises uridine residues. In some embodiments, at least 5% of uridine residues in the polyribonucleotide are 5-hydroxymethyluridine. In some embodiments, less than 100% of uridine residues in the polyribonucleotide are 5-hydroxymethyluridine. In some embodiments, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 99% of uridine residues in the polyribonucleotide are 5-hydroxymethyluridine. In some embodiments, more than 60% of uridine residues in the polyribonucleotide are 5-hydroxymethyluridine.

In some embodiments, a polyribonucleotide disclosed herein comprises one or more modified nucleobases comprising: N1-methylpseudouracil, a pyridin-4-one, 5-aza-uracil, 6-aza-uracil, 2-thio-5-aza-uracil, 2-thio-uracil, 5-methyl cytosine, 5-aza-cytosine, 6-aza-cytosine, pseudoisocytosine, 3-methyl-cytosine, 5-formyl-cytosine, N4-methyl-cytosine, a 2-amino-purine, a 2,6-diaminopurine, a 2-amino-6-halo-purine, a 6-halo-purine, hypoxanthine, 1-methyl-hypoxanthine, 4,6-dimethyl-3,3a,4,9a-tetrahydro-9H-imidazo[1,2-a]purin-9-one, and 4,6,7-trimethyl-3,3a,4,9a-tetrahydro-9H-imidazo[1,2-a]purin-9-one.

Modified Ribose in Polyribonucleotides Disclosed Herein

Polynucleotides disclosed herein can be a polyribonucleotide which further comprises one or more modified ribonucleotides comprising: a modified nucleobase, a modified ribose, a modified backbone, or any combination thereof.

In some embodiments, a polynucleotide is a polyribonucleotide. In some embodiments, a polyribonucleotide comprises one or more modified ribonucleotides. In some embodiments, a polyribonucleotide comprises a modified ribose.

In some embodiments, one or more modified ribonucleotides comprises a modified ribose. In some such embodiments, a modified ribose is 2'-O-acetyl ribose.

In some embodiments, a modified ribonucleotide comprises:

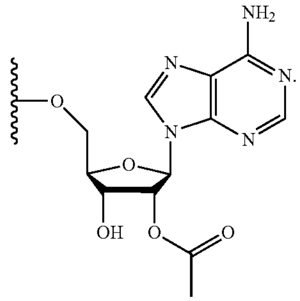

In some embodiments, a modified ribonucleotide comprises:

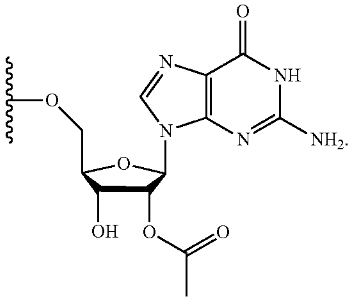

In some embodiments, a modified ribonucleotide comprises:

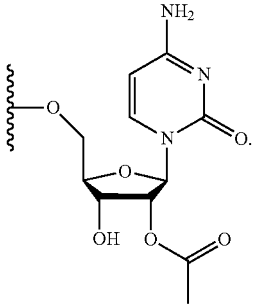

In some embodiments, a modified ribonucleotide comprises:

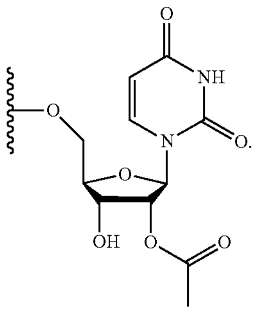

In some embodiments, a modified ribonucleotide comprises:

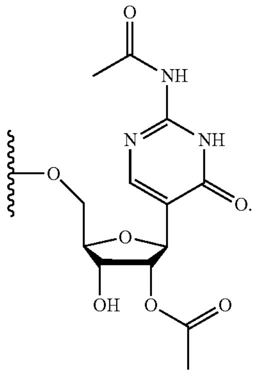

In some embodiments, a modified ribonucleotide comprises:

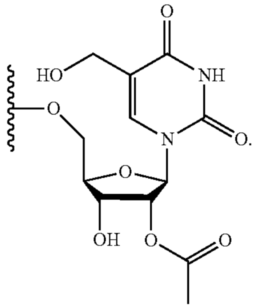

In some embodiments, a modified ribonucleotide comprises:

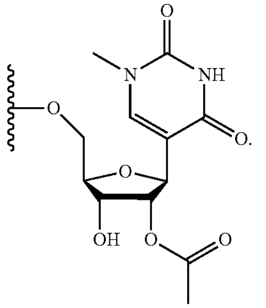

In some embodiments, at least 5% of ribose moieties of a polynucleotide are 2'-O-acetyl ribose.

In some embodiments, about 5% to about 99% of ribose moieties of a polynucleotide are 2'-O-acetyl ribose.

In some embodiments, a polyribonucleotide disclosed herein comprises a cap structure comprising an acetyl group.

In some embodiments, a polyribonucleotide disclosed herein comprises a cap structure and a cap structure comprises a 2'-O-acetyl ribose.

In some embodiments, a polyribonucleotide disclosed herein further comprises one or more ribonucleotides that does not comprise a 2'-O acetyl ribose.

Polyribonucleotides and Payloads Disclosed Herein

Among other things, the present disclosure provides polyribonucleotides comprising a cap structure described at the 5' end. In some embodiments, a polyribonucleotide comprising a cap structure disclosed herein at the 5' end is or comprises a messenger RNA (mRNA). In some embodiments, a polyribonucleotide comprising a cap structure disclosed herein at the 5' end is or comprises a gRNA. In some embodiments, a polyribonucleotide comprising a cap structure disclosed herein at the 5' end is or comprises an inhibitory RNA. In some embodiments, a polyribonucleotide comprising a cap structure disclosed herein at the 5' end is or comprises an miRNA or siRNA. In some embodiments, a polyribonucleotide comprising a cap structure disclosed herein at the 5' end is or comprises an antisense oligonucleotide. In some embodiments, a polyribonucleotide comprising a cap structure disclosed herein at the 5' end is or comprises a long non-coding RNA.

In many embodiments, a polyribonucleotide disclosed herein comprising a cap structure described comprises a sequence encoding a coding region. In some embodiments, a coding region described herein encodes a gene product, e.g., a payload. In some embodiments, a gene product described herein, e.g., a payload, is or comprises a polypeptide. In some embodiments, a gene product described herein, e.g., a payload is or comprises an RNA situated in a polypeptide.

In some embodiments, a payload described herein is or comprises an antigen, an enzyme, an antibody or a fragment thereof, a secreted protein, a cell surface protein, or a helper protein, or a fragment or variant of any of the foregoing. In some embodiments, a payload is an antigen or a fragment or variant thereof. In some embodiments, a payload is an antigen or an immunogenic fragment or an immunogenic variant thereof.

Payloads Comprising Sbi Domains

In some embodiments, a polyribonucleotide comprising a cap structure described herein comprises a sequence encoding a fusion polypeptide. In some embodiments, a polyribonucleotide described herein encodes a fusion polypeptide payload. In some embodiments, a fusion polypeptide comprises (a) an antigen or an immunogenic fragment or an immunogenic variant thereof; and (b) a complement $C_3$d-binding polypeptide from an immunoglobulin-binding protein (Sbi) of *Staphylococcus aureus*. In some embodiments, an Sbi complement C3d-binding polypeptide comprises Sbi domain III and/or Sbi domain IV. Exemplary SBi domain III and Sbi domain IV polypeptide sequences are provided herein.

*S. aureus* binder of immunoglobulin (Sbi) is an exemplary polypeptide which can bind complement C3d (as described in Clark et al. (2011) *Mol Immunol.* 48 (4): 452-462, the entire contents of which is incorporated herein by reference). Sbi comprises two immunoglobulin binding domains (Domains I and II) and two complement $C_3$d binding domains (Domains III and IV). Sbi domains III and IV can bind C3d (in native C3, iC3b and C3dg) and can result in fluid phase consumption of C3 via activation of the alternative pathway (see Clark et al 2011). It has also been shown that Sbi can be secreted and is involved in *S. aureus* immune evasion (Burman et al., 2008 *J. Biol. Chem;* 283:17579-17593).

Without wishing to be bound by theory, it is believed that in some embodiments, a complement $C_3$d-binding polypeptide from Sbi of *S. aureus* can be used as an adjuvant to enhance and/or modulate an immune response from an antigen described herein while dampening an unwanted immune response from the polyribonucleotide itself. In some embodiments, the immune response is elicited by an antigen or a fragment or variant thereof, as disclosed herein. In some embodiments, the immune response is elicited by a component of Sbi of *S. aureus*.

Methods of generating and using a fusion polypeptide comprising an Sbi domain III and/or IV is described in U.S. Pat. No. 11,771,758, which is herein incorporated by reference in its entirety.

In some embodiments, any of the fusion polypeptides, fusion polynucleotides, compositions, methods or uses disclosed herein, comprises a complement C3d-binding polypeptide of Sbi of *S. aureus*. In some embodiments, a Sbi complement C3d binding polypeptide comprises one or both of domain III and domain IV of Sbi, or a functional fragment or a functional variant thereof.

In some embodiments, a domain III of Sbi from *S. aureus* strain Mu50 is provided herein as SEQ ID NO: 3.

IENADKAIKDFQDNKAPHDKSAAYEANSK-LPKDLRDKNNRFV

In some embodiments, a domain IV of Sbi from *S. aureus* strain Mu50 is provided herein as SEQ ID NO: 4.

EKVSIEKAIVRHDERVKSANDAISKL-NEKDSIENRRLAQREVNKAPMDVKEHL QKQLD

In some embodiments, a Sbi complement C3d binding polypeptide comprises an amino acid sequence having at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 3. In some embodiments, a Sbi complement C3d binding polypeptide comprises an amino acid sequence having at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 3. In some embodiments, a Sbi complement C3d binding polypeptide comprises an amino acid sequence having at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 3.

In some embodiments, a Sbi complement C3d binding polypeptide is encoded by a polynucleotide which encodes an amino acid having at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 4. In some embodiments, a Sbi complement C3d binding polypeptide is encoded by a polynucleotide which encodes an amino acid having at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 4. In some embodiments, a Sbi complement C3d binding polypeptide is encoded by a polynucleotide which encodes an amino acid having at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 4. Due to degeneracy in the genetic code, those of ordinary skill in the art would understand that other DNA sequences (including codon-optimized sequences) could encode these polypeptides, as well as the others disclosed herein.

In some embodiments, a payload comprises a fusion polypeptide comprising an antigen or a fragment or variant thereof, and a complement C3d-binding polypeptide comprising an Sbi domain III. In some embodiments, an Sbi domain III comprises an amino acid sequence having at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 3. In some embodiments, an Sbi domain III comprises the amino acid sequence of SEQ ID NO: 3.

In some embodiments, a payload comprises a fusion polypeptide comprising an antigen or a fragment or variant thereof, and a complement C3d-binding polypeptide comprising an Sbi domain IV. In some embodiments, an Sbi domain IV comprises an amino acid sequence having at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 4. In some embodiments, an Sbi domain IV comprises the amino acid sequence of SEQ ID NO: 4.

In some embodiments, a payload comprises a fusion polypeptide comprising an antigen or a fragment or variant thereof, and a complement C3d-binding polypeptide comprising an Sbi domain III and an Sbi domain IV. In some embodiments, an Sbi domain III comprises an amino acid sequence having at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 3. In some embodiments, an Sbi domain III comprises the amino acid sequence of SEQ ID NO: 3. In some embodiments, an Sbi domain IV comprises an amino acid sequence having at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 4. In some embodiments, an Sbi domain IV comprises the amino acid sequence of SEQ ID NO: 4.

Method of Making Polyribonucleotides

This disclosure provides, among other things, methods of making a polyribonucleotide disclosed herein. In some embodiments, disclosed herein is method of producing a polyribonucleotide comprising a step of incubating an in vitro transcription mixture, wherein the in vitro transcription mixture comprises: (i) a DNA template; (ii) at least one RNA polymerase or a variant or a fragment thereof; and (iii) a plurality of ribonucleotides.

Also disclosed herein are in vitro transcription mixtures useful in producing a polyribonucleotide disclosed herein. In some embodiments, disclosed herein is in vitro transcription mixture comprising: (i) a DNA template; (ii) at least one RNA polymerase or a variant or a fragment thereof; and (iii) a plurality of ribonucleotides.

In some embodiments, a method or an in vitro transcription mixture produces a plurality of polyribonucleotides.

In some embodiments, an RNA polymerase comprises: a bacteriophage RNA polymerase, a mitochondrial RNA polymerase, a eukaryotic RNA polymerase, a bacterial RNA polymerase, or any combination thereof. In some embodiments, an RNA polymerase comprises a T7 RNA polymerase, a T3 RNA polymerase, a SP6 RNA polymerase, a viral RNA polymerase, a N4 virion RNA polymerase, or a variant of any of the foregoing.

In some embodiments, a polyribonucleotide produced by a method disclosed herein or using an in vitro transcription mixture comprises a coding region. In some embodiments, a coding region encodes a gene product, e.g., as described herein.

In some embodiments, a polyribonucleotide produced by a method disclosed herein or using an in vitro transcription mixture does not comprise a coding region. In some embodiments, a polyribonucleotide which does not comprises a coding region can also be referred to as a non-coding RNA. Exemplary non-coding RNA include, but are not limited to, long non-coding RNAS (lncRNA), microRNAs, siRNAs, piRNAs, snoRNAs, snRNAs, exRNAs, scaRNAs rRNA, and tRNA, In some embodiments, a polyribonucleotide produced by a method disclosed herein or using an in vitro transcription mixture comprises a guide RNA, an siRNA, a microRNA, a long non-coding RNA, or a messenger RNA (mRNA), or any combination thereof.

In some embodiments, a polyribonucleotide produced by a method disclosed herein or using an in vitro transcription mixture comprises a modified nucleobase, a modified ribose, a modified backbone, or any combination thereof. In some embodiments, a polyribonucleotide further comprises at the 5' end a compound having the Formula II:

II

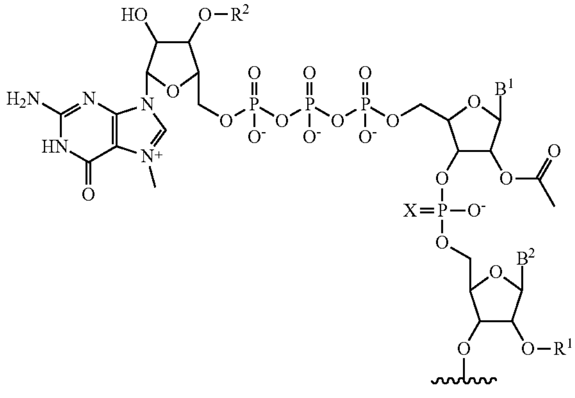

or a salt thereof, wherein:

- ∿∿∿ indicates the position at which the compound is attached to the polyribonucleotide;
- each of $B^1$ and $B^2$ is independently selected from a natural base and a modified base;
- $R^1$ is selected from hydrogen, $C_{1-6}$ alkyl, and —C(=O)$CH_3$;
- $R^2$ is hydrogen or —$CH_3$; and
- X is O or S.

In some embodiments, a polyribonucleotide produced by a method disclosed herein or using an in vitro transcription mixture encodes a payload. In some embodiments, a payload comprises one or more target polypeptides. In some embodiments, a payload comprises an RNA situated in a polyribonucleotide.

In some embodiments of a method of producing a polyribonucleotide disclosed herein, an incubating step occurs at a temperature of at least 37° C.

In some embodiments of a method of producing a polyribonucleotide disclosed herein, an incubating step occurs at a temperature of no more than about 55° C.

In some embodiments of a method of producing a polyribonucleotide disclosed herein, an incubating step occurs at a temperature of about 45° C., about 46° C., about 47° C., about 48° C., about 49° C., about 50° C., about 51° C., about 52° C., about 53° C., about 54° C., about 55° C., or higher. In some embodiments of a method of producing a polyribonucleotide disclosed herein, an incubating step occurs at a temperature of about 45° C., about 46° C., about 47° C., about 48° C., about 49° C., about 50° C., about 51° C., about 52° C., about 53° C., about 54° C., or about 55° C. In some embodiments of a method of producing a polyribonucleotide disclosed herein, an incubating step occurs at a temperature of 45° C., 46° C., 47° C., 48° C., 49° C., 50° C., 51° C., 52° C., 53° C., 54° C., or 55° C.

In some embodiments of a method of producing a polyribonucleotide disclosed herein, an incubating step occurs at a temperature of about 45° C. to about 55° C., about 46° C. to about 55° C., about 47° C. to about 55° C., about 48° C. to about 55° C., about 49° C. to about 55° C., about 50° C. to about 55° C., about 51° C. to about 55° C., about 52° C. to about 55° C., about 53° C. to about 55° C., about 54° C. to about 55° C., about 45° C. to about 54° C., about 45° C. to about 53° C., about 45° C. to about 52° C., about 45° C. to about 51° C., about 45° C. to about 50° C., about 45° C. to about 49° C., about 45° C. to about 48° C., about 45° C. to about 47° C., or about 45° C. to about 46° C.

In some embodiments of a method of producing a polyribonucleotide disclosed herein, an incubating step is performed for at least 1 hour, at least 2 hours, at least 3 hours, at least 4 hours or longer.

In some embodiments method of producing a polyribonucleotide disclosed herein, an incubating step is performed at a pH of: about 5 to about 8, about 5 to about 7.9, about 5 to about 7.8, about 5 to about 7.7, about 5 to about 7.6, about 5 to about 7.5, about 5 to about 7.4, about 5 to about 7.3, about 5 to about 7.2, about 5 to about 7.1, about 5 to about 7.0, about 5 to about 6.9, about 5 to about 6.8, about 5 to about 6.7, about 5 to about 6.6, about 5 to about 6.5, about 5 to about 6.4, about 5 to about 6.3, about 5 to about 6.2, about 5 to about 6.1, about 5 to about 6.0, about 5 to about 5.9, about 5 to about 5.8, about 5 to about 5.7, about 5 to about 5.6, about 5 to about 5.5, about 5 to about 5.4, about 5 to about 5.3, about 5 to about 5.2, about 5 to about 5.1, or about 5.1 to about 8, about 5.2 to about 8, about 5.3 to about 8, about 5.4 to about 8, about 5.5 to about 8, about 5.6 to about 8, about 5.7 to about 8, about 5.8 to about 8, about 5.9 to about 8, about 6.0 to about 8, about 6.1 to about 8, about 6.2 to about 8, about 6.3 to about 8, about 6.4 to about 8, about 6.5 to about 8, about 6.6 to about 8, about 6.7 to about 8, about 6.8 to about 8, about 6.9 to about 8, about 7.0 to about 8, about 7.1 to about 8, about 7.2 to about 8, about 7.3 to about 8, about 7.4 to about 8, about 7.5 to about 8, about 7.6 to about 8, about 7.7 to about 8, about 7.8 to about 8, or about 7.9 to about 8.

In some embodiments method of producing a polyribonucleotide disclosed herein, an incubating step is performed at a pH of about 5, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, or about 8.0.

In some embodiments method of producing a polyribonucleotide disclosed herein, an incubating step is performed at a pH of: 5 to 8, 5 to 7.9, 5 to 7.8, 5 to 7.7, 5 to 7.6, 5 to 7.5, 5 to 7.4, 5 to 7.3, 5 to 7.2, 5 to 7.1, 5 to 7.0, 5 to 6.9, 5 to 6.8, 5 to 6.7, 5 to 6.6, 5 to 6.5, 5 to 6.4, 5 to 6.3, 5 to 6.2, 5 to 6.1, 5 to 6.0, 5 to 5.9, 5 to 5.8, 5 to 5.7, 5 to 5.6, 5 to 5.5, 5 to 5.4, 5 to 5.3, 5 to 5.2, 5 to 5.1, or 5.1 to 8, 5.2 to 8, 5.3 to 8, 5.4 to 8, 5.5 to 8, 5.6 to 8, 5.7 to 8, 5.8 to 8, 5.9 to 8, 6.0 to 8, 6.1 to 8, 6.2 to 8, 6.3 to 8, 6.4 to 8, 6.5 to 8, 6.6 to 8, 6.7 to 8, 6.8 to 8, 6.9 to 8, 7.0 to 8, 7.1 to 8, 7.2 to 8, 7.3 to 8, 7.4 to 8, 7.5 to 8, 7.6 to 8, 7.7 to 8, 7.8 to 8, or 7.9 to 8.

In some embodiments method of producing a polyribonucleotide disclosed herein, an incubating step is performed at a pH of 5, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, or 8.0.

In some embodiments, methods of producing a polyribonucleotide disclosed herein further comprises use of an osmolyte. In some embodiments, an in vitro transcription mixture disclosed herein, e.g., for use in a method of making a polyribonucleotide, further comprises an osmolyte. In some embodiments, an osmolyte is an amino acid-based osmolyte. In some embodiments, an amino acid-based osmolyte comprises a glycine-based osmolyte. In some embodiments, a glycine-based osmolyte comprise betaine.

RNA Formulations

Among other things, provided herein are compositions comprising a polyribonucleotide disclosed herein, and formulations thereof. In some embodiments, a composition comprising a polyribonucleotide disclosed herein is formulated in a lipid nanoparticle (LNP) formulation.

In some embodiments, a polyribonucleotide disclosed herein encodes for a polypeptide. In some embodiments, a polyribonucleotide disclosed herein is or comprises a messenger RNA. In some embodiments, a composition comprising a polyribonucleotide comprising a messenger RNA is formulated in a lipid nanoparticle (LNP) formulation.

In some embodiments, a polyribonucleotide disclosed herein is or comprises a gRNA. In some embodiments, a composition comprising a polyribonucleotide comprising a gRNA is formulated in a lipid nanoparticle (LNP) formulation.

In some embodiments, a polyribonucleotide disclosed herein is or comprises an inhibitory RNA. In some embodiments, a composition comprising a polyribonucleotide comprising an inhibitory RNA is formulated in a lipid nanoparticle (LNP) formulation.

In some embodiments, a polyribonucleotide disclosed herein is or comprises an miRNA or siRNA. In some embodiments, a composition comprising a polyribonucleotide comprising a miRNA or siRNA is formulated in a lipid nanoparticle (LNP) formulation.

In some embodiments, a polyribonucleotide disclosed herein is or comprises an antisense oligonucleotide. In some embodiments, a composition comprising a polyribonucleotide comprising an antisense oligonucleotide is formulated in a lipid nanoparticle (LNP) formulation.

In some embodiments, the disclosure provides an LNP formulation comprising a polyribonucleotide disclosed herein for use in a pharmaceutical composition, e.g., an immunogenic composition.

Methods of Using Compositions Disclosed Herein

The disclosure provides, among other things, methods for using a polyribonucleotide disclosed herein, or a composition comprising the same.

In some embodiments, provided herein is a method of administering a polyribonucleotide disclosed herein or a composition comprising a polyribonucleotide disclosed herein to a cell, tissue or subject.

In some embodiments, provided herein is a vaccination method comprising administering a polyribonucleotide disclosed herein or a composition comprising a polyribonucleotide disclosed herein to a cell, tissue or subject.

In some embodiments, disclosed herein is a gene therapy method comprising administering a polyribonucleotide disclosed herein or a composition comprising a polyribonucleotide disclosed herein to a cell, tissue or subject. In some embodiments, a gene therapy method comprises delivery of one or more components of a gene therapy, e.g., a guide RNA and/or a Cas polypeptide.

In some embodiments, provided herein is a method for stimulating an immune response comprising administering a polyribonucleotide disclosed herein or a composition comprising a polyribonucleotide disclosed herein to a cell, tissue or subject.

In some embodiments, also provided herein is a cell therapy engineering method comprising administering a polyribonucleotide disclosed herein or a composition comprising a polyribonucleotide disclosed herein to a cell, tissue or subject.

In some embodiments, provided herein is an immunotherapy method comprising administering a polyribonucleotide disclosed herein or a composition comprising a polyribonucleotide disclosed herein to a cell, tissue or subject. In some embodiments, an immunotherapy method comprises delivery of an antibody therapy and/or an immune checkpoint therapy.

In some embodiments, disclosed herein is a protein replacement therapy method comprising administering a polyribonucleotide disclosed herein or a composition comprising a polyribonucleotide disclosed herein to a cell, tissue or subject. In some embodiments, a protein replacement therapy comprises delivery of an enzyme replacement therapy.

In some embodiments, provided herein is a chemotherapeutic method comprising administering a polyribonucleotide disclosed herein or a composition comprising a polyribonucleotide disclosed herein to a cell, tissue or subject.

In some embodiments, a method or use disclosed herein comprises determining cell viability of a cell, tissue or subject. In some embodiments, cell viability is a measure of a length of time one or more cells of a cell, tissue or subject live. In some embodiments, cell viability is a measure of a number of cells of a cell, tissue or subject alive at one or more time points.

In some embodiments, a cell, tissue or subject to which a polyribonucleotide or a composition comprising the same has been administered exhibits improved cell viability as compared to a reference cell viability. In some embodiments, a reference cell viability is a cell viability of a cell, tissue or subject that has been administered a comparable polyribonucleotide or a composition comprising the same that includes fewer 2'-O-acetylated ribose (e.g., does not include any 2'-O-acetyl ribose) compared to a polyribonucleotide disclosed herein.

In some embodiments, a method or use disclosed herein further comprises determining an immune system response of a cell, tissue or subject to which a polyribonucleotide or a composition comprising the same has been administered. In some embodiments, an immune response comprises an innate immune system response comprising innate immune system induced toxicity. In some embodiments, determining an innate immune system response comprises determining a level and/or activation of NF-κB or an NF-κB pathway; IRF or an IRF pathway; or inflammatory cytokines, or any combination thereof in a cell, tissue or subject. In some embodiments, determining an innate immune system response comprises determining a level of uncapped RNA detection in a cell, tissue or subject.

In some embodiments, a cell, tissue or subject to which a polyribonucleotide or a composition comprising the same has been administered exhibits a reduced innate immune system response as compared to a reference. In some embodiments, a reference is an innate immune system response of a cell, tissue or subject that has been administered a comparable polyribonucleotide that does not include a compound disclosed herein.

In some embodiments, a method or use disclosed herein further comprises determining efficacy of a polyribonucleotide or a composition comprising the same in a cell, tissue or subject to which a polyribonucleotide or a composition comprising the same has been administered.

In some embodiments, determining efficacy comprises determining an antibody response or cellular response in a cell, tissue or subject. In some embodiments, a cell, tissue or subject to which a polyribonucleotide or a composition comprising the same has been administered exhibits an increased antibody response or cellular response as compared to a reference. In some embodiments, a reference is an antibody response or cellular response of a cell, tissue or subject that has been administered a comparable polyribonucleotide that does not include a compound disclosed herein.

In some embodiments, a method or use disclosed herein comprises administering a polyribonucleotide or a composition comprising the same to a cell, tissue or subject at least two times. In some embodiments, a method disclosed herein comprises administering a polyribonucleotide or a composition comprising the same to a cell, tissue or subject at least 2 times, at least 3 times, at least 4 times, at least 5 times, at least 6 times, at least 7 times, at least 8 times, at least 9 times or at least 10 times.

In some embodiments, a method or use disclosed herein comprises administering a plurality of doses of a polyribonucleotide or a composition comprising the same to a cell, tissue or subject. In some embodiments, a second or subsequent dose of a polyribonucleotide or a composition comprising the same has a substantially similar efficacy in a cell, tissue, or subject compared to administration of a first dose of a composition comprising a polyribonucleotide.

In some embodiments of any of the methods or uses disclosed herein, a polyribonucleotide or a composition comprising the same is administered to a cell, tissue or subject at a higher dose compared to an appropriate reference comparator. In some embodiments, a reference comparator comprise a comparable polyribonucleotide that does not include a compound disclosed herein.

In some embodiments of any of the methods or uses disclosed herein, the composition is administered via any one of the following routes of administration: intramuscular, intravenous, subcutaneous, intrathecal, intradermal, ocular, intranasal, sublingual, or oral.

In some embodiments of any of the methods or uses disclosed herein a cell is a mammalian cell.

In some embodiments of any of the methods or uses disclosed herein a tissue is a mammalian tissue.

In some embodiments of any of the methods or uses disclosed herein, a subject is a mammal. In some embodiments, a mammal is a human.

Kits

Another aspect of the present disclosure further provides a pharmaceutical pack or kit. In some embodiments, a kit can comprise a polyribonucleotide or a composition described herein. In some embodiment, kits may be used in any applicable method, e.g., methods as described herein.

ENUMERATED EMBODIMENTS

Embodiment 1. A compound of Formula I:

I

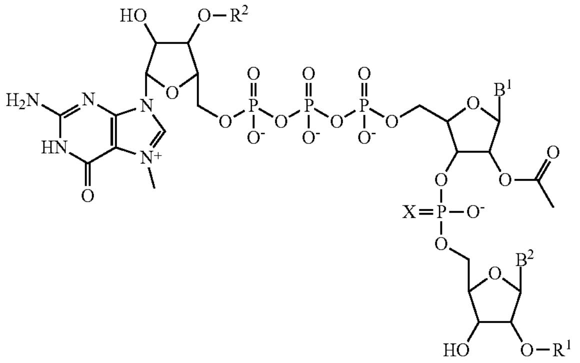

or a salt thereof, wherein:

each of $B^1$ and $B^2$ is independently selected from a natural base and a modified base;

$R^1$ is selected from hydrogen, $C_{1-6}$ alkyl, and —C(=O)$CH_3$;

$R^2$ is hydrogen or —$CH_3$; and

X is O or S.

Embodiment 2. The compound of embodiment 1, wherein the compound is selected from Formulae I-a, I-b, I-c, I-d, I-e, and I-f:

I-a

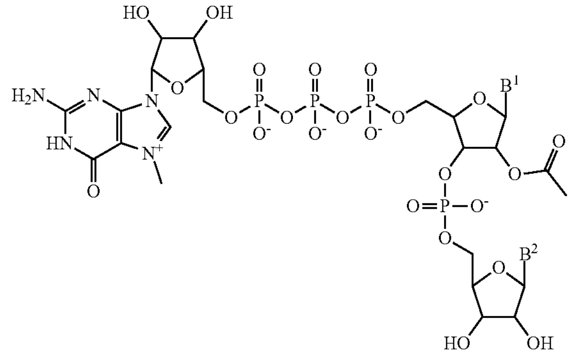

I-b

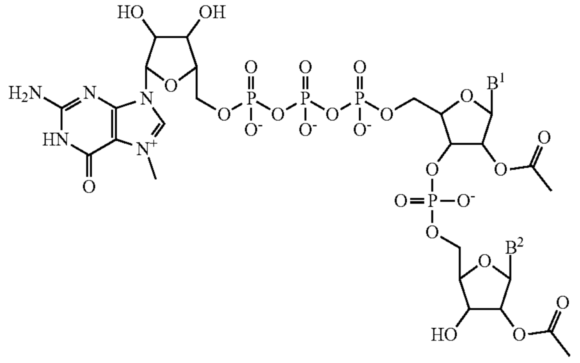

-continued

I-c

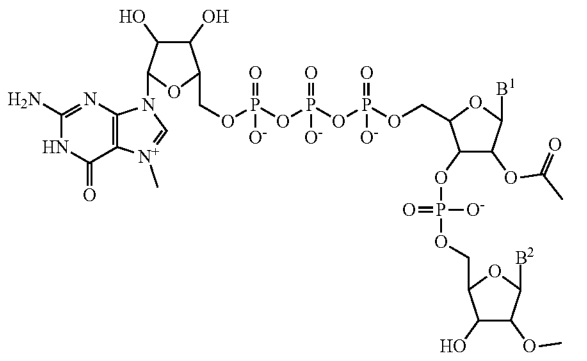

I-d

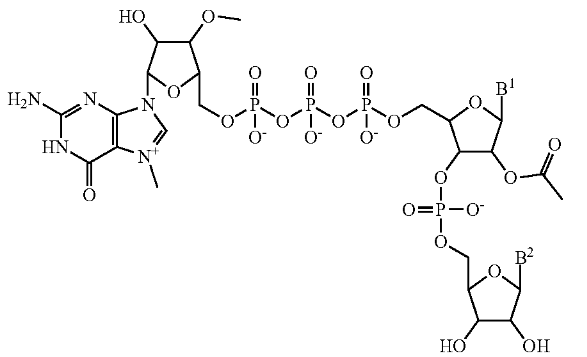

I-e

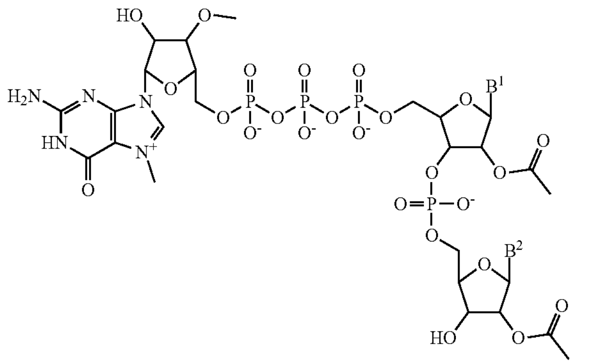

I-f

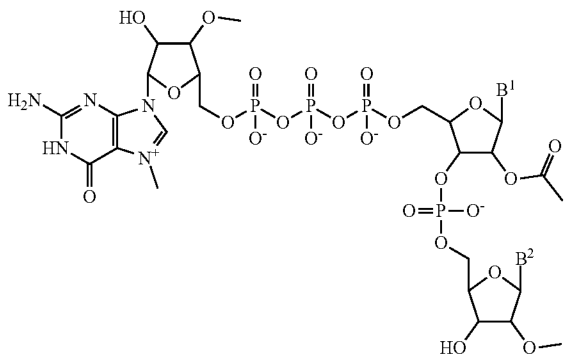

or a salt thereof.

Embodiment 3. The compound according to embodiment 1, wherein $R^1$ is hydrogen.

Embodiment 4. The compound according to embodiment 1, wherein $R^1$ is $C_{1-6}$ alkyl.

Embodiment 5. The compound according to embodiment 4, wherein $R^1$ is $—CH_3$.

Embodiment 6. The compound according to embodiment 1, wherein $R^1$ is $—C(=O)CH_3$.

Embodiment 7. The compound according to any one of embodiments 1 or 3-6, wherein X is O.

Embodiment 8. The compound according to any one of embodiments 1 or 3-6, wherein X is S.

Embodiment 9. The compound according to any one of embodiments 1-8, wherein $B^1$ and/or $B^2$ is a modified base is selected from N1-methylpseudouracil, a pyridin-4-one, 5-aza-uracil, 6-aza-uracil, 2-thio-5-aza-uracil, 2-thio-uracil, 5-methyl cytosine, 5-aza-cytosine, 6-aza-cytosine, pseudoisocytosine, 3-methyl-cytosine, 5-formyl-cytosine, N4-methyl-cytosine, a 2-amino-purine, a 2,6-diaminopurine, a 2-amino-6-halo-purine, a 6-halo-purine, hypoxanthine, 1-methyl-hypoxanthine, 4,6-dimethyl-3,3a,4,9a-tetrahydro-9H-imidazo[1,2-a]purin-9-one, 4,6,7-trimethyl-3,3a,4,9a-tetrahydro-9H-imidazo[1,2-a]purin-9-one, N4-acetylcytosine, and hydroxymethyluracil.

Embodiment 10. The compound according to any one of embodiments 1-8, wherein $B^1$ and/or $B^2$ is a natural base is selected from guanine, adenine, cytosine, and uracil.

Embodiment 11. A polyribonucleotide comprising one or more modified ribonucleotides comprising: a modified nucleobase, a modified ribose, a modified backbone, or any combination thereof.

Embodiment 12. The polyribonucleotide of embodiment 11, wherein the one or more modified ribonucleotides comprises a modified nucleobase, wherein the modified nucleobase is N4-acetylcytosine:

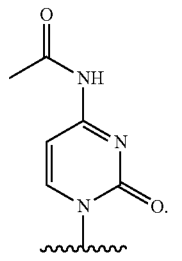 [SMILES: *n1ccc(NC(C)=O)nc1=O]

Embodiment 13. The polyribonucleotide of embodiment 11, wherein the one or more modified ribonucleotides comprises a modified nucleobase, wherein the modified nucleobase is 5-hydroxymethyluracil:

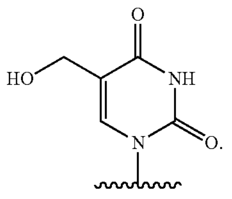 [SMILES: *n1cc(CO)c(=O)[nH]c1=O]

Embodiment 14. The polyribonucleotide of embodiment 11, wherein the one or more modified ribonucleotides comprises one or more modified nucleobases selected from: N1-methylpseudouracil, a pyridin-4-one, 5-aza-uracil, 6-aza-uracil, 2-thio-5-aza-uracil, 2-thio-uracil, 5-methyl cytosine, 5-aza-cytosine, 6-aza-cytosine, pseudoisocytosine, 3-methyl-cytosine, 5-formyl-cytosine, N4-methyl-cytosine, a 2-amino-purine, a 2,6-diaminopurine, a 2-amino-6-halopurine, a 6-halo-purine, hypoxanthine, 1-methyl-hypoxanthine, 4,6-dimethyl-3,3a,4,9a-tetrahydro-9H-imidazo[1,2-a]purin-9-one, and 4,6,7-trimethyl-3,3a,4,9a-tetrahydro-9H-imidazo[1,2-a]purin-9-one.

Embodiment 15. The polyribonucleotide of embodiment 11, wherein the one or more modified ribonucleotides comprises a modified ribose, wherein the modified ribose is 2'-O-acetyl ribose.

Embodiment 16. The polyribonucleotide of any one of embodiments 12-14, wherein the one or more modified ribonucleotides further comprises a modified ribose, wherein the modified ribose is 2'-O-acetyl ribose.

Embodiment 17. The polynucleotide of embodiment 15, wherein the one or more modified ribonucleotides comprises

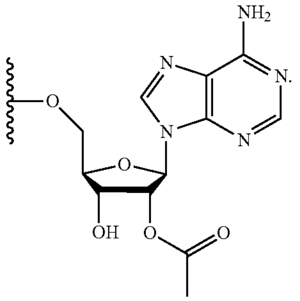

Embodiment 18. The polynucleotide of embodiment 15, wherein the one or more modified ribonucleotides comprises

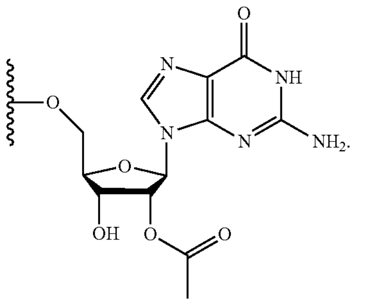

Embodiment 19. The polynucleotide of embodiment 15, wherein the one or more modified ribonucleotides comprises

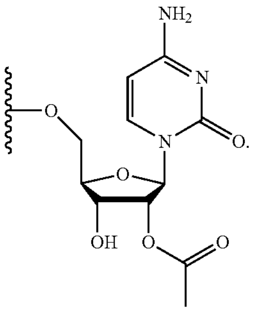

Embodiment 20. The polynucleotide of embodiment 15, wherein one or more modified ribonucleotides comprises

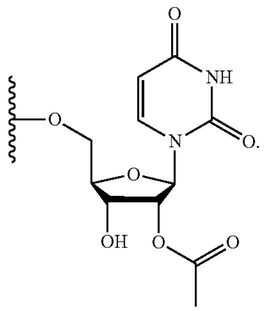

Embodiment 21. The polynucleotide of embodiment 12, wherein the one or more modified ribonucleotides comprises

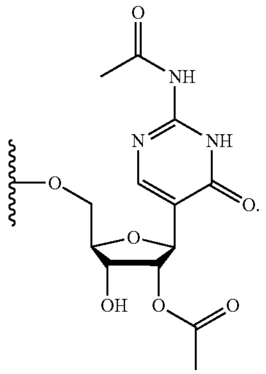

Embodiment 22. The polynucleotide of embodiment 13, wherein the one or more modified ribonucleotides comprises

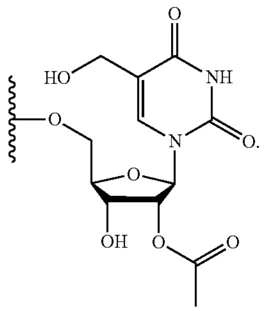

Embodiment 23. The polynucleotide of embodiment 15, wherein the one or more modified ribonucleotides comprises

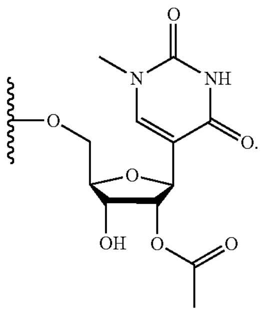

Embodiment 24. The polyribonucleotide of any one of embodiments 12-14, wherein the one or more modified ribonucleotides further comprises a modified ribose, wherein the modified ribose comprises a 2'-O-acetyl group.

Embodiment 25. The polyribonucleotide according to any one of embodiments 11-24, wherein the polyribonucleotide further comprises at the 5' end a compound having the Formula II:

II

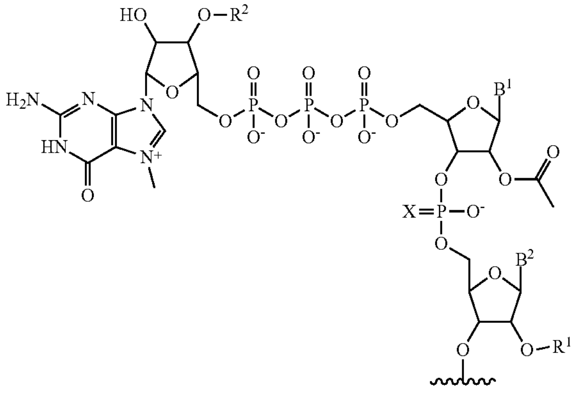

or a salt thereof, wherein:

- ∿∿∿ indicates the position at which the compound is attached to the polyribonucleotide;
- each of $B^1$ and $B^2$ is independently selected from a natural base and a modified base;
- $R^1$ is selected from hydrogen, $C_{1-6}$ alkyl, and —C(═O)$CH_3$;
- $R^2$ is hydrogen or —$CH_3$; and
- X is O or S.

Embodiment 26. The polyribonucleotide according to embodiment 25, wherein the compound is selected from any of Formulae II-a, II-b, II-c, II-d, II-e, and II-f:

II-a

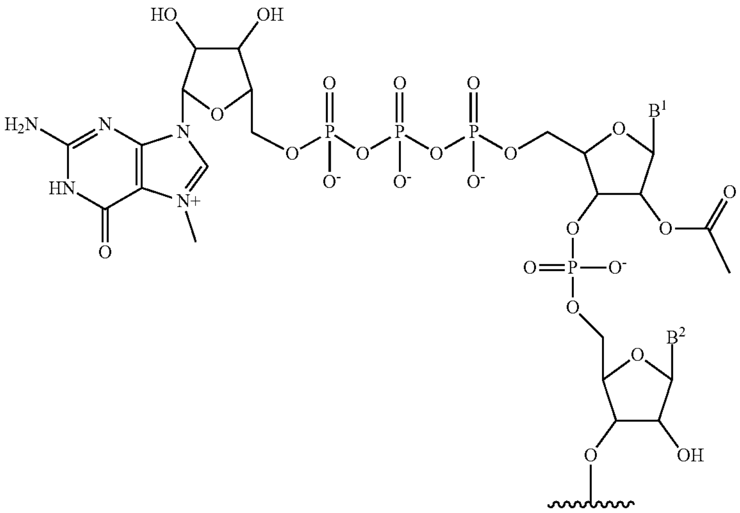

-continued
II-b
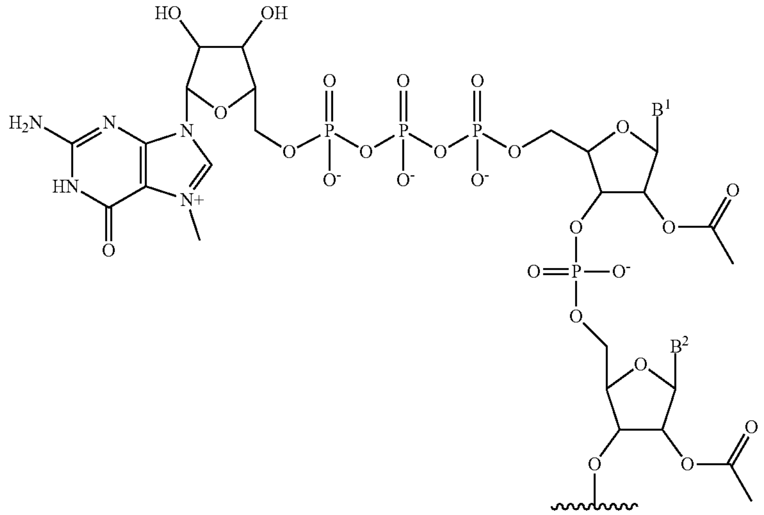
II-c
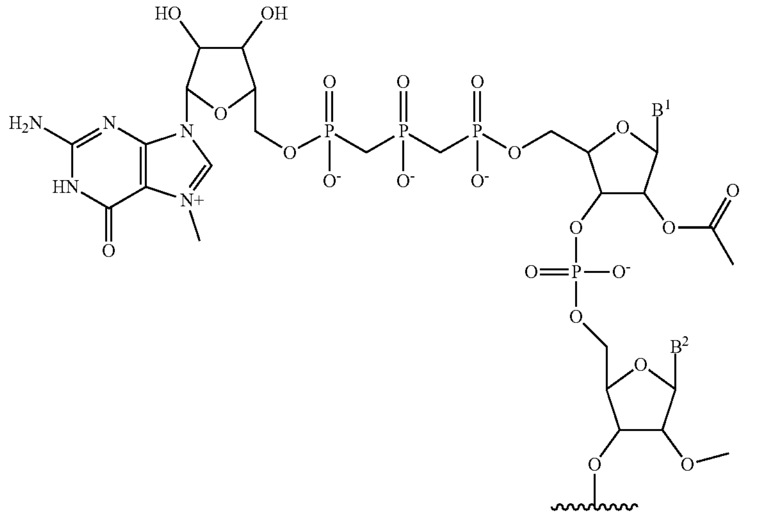
II-d
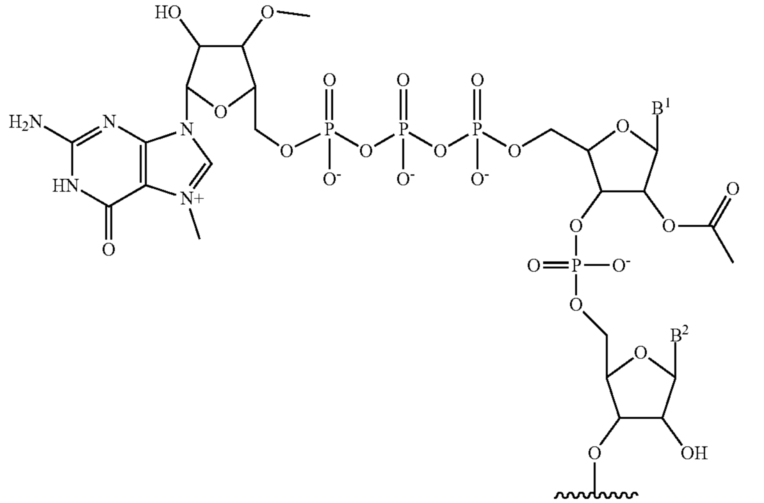

-continued
II-e
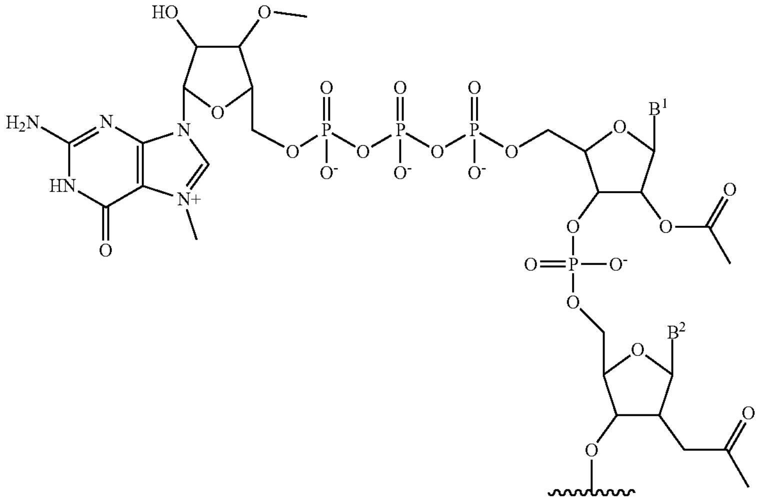
II=f
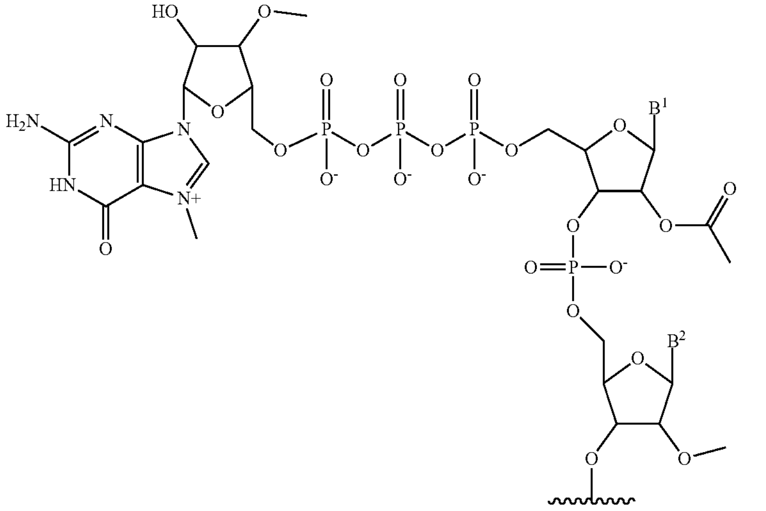
or a salt thereof.
Embodiment 27. A polyribonucleotide comprising at the 5' end a compound having the Formula II:
II
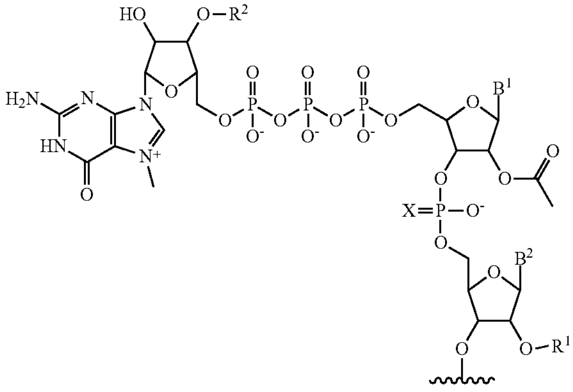
or a salt thereof, wherein:

∿∿∿ indicates the position at which the compound is attached to the polyribonucleotide;

each of $B^1$ and $B^2$ is independently selected from a natural base and a modified base;

$R^1$ is selected from hydrogen, $C_{1-6}$ alkyl, and —C(═O)$CH_3$;

$R^2$ is hydrogen or —$CH_3$; and

X is O or S.

Embodiment 28. The polyribonucleotide according to embodiment 27, wherein the compound is selected from any of Formulae II-a, II-b, II-c, II-d, II-e, and II-f:

II-a

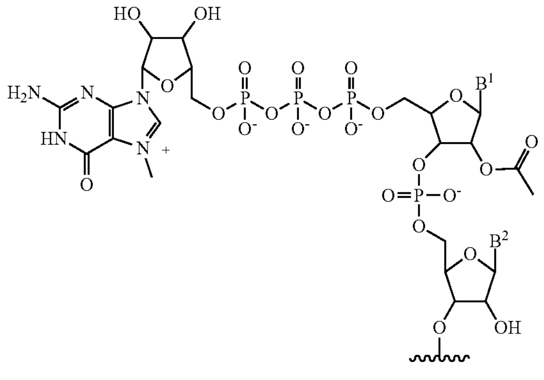

II-b

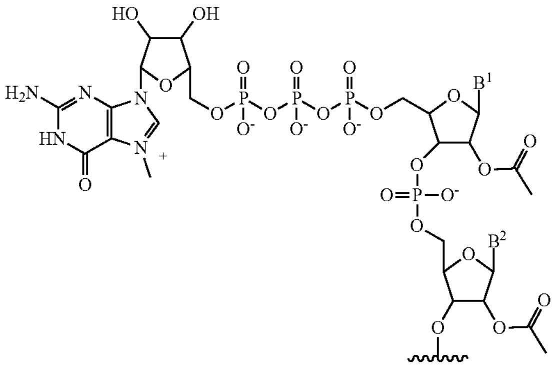

II-c

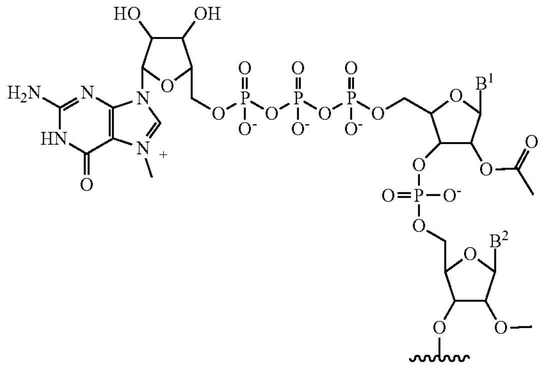

-continued

II-d

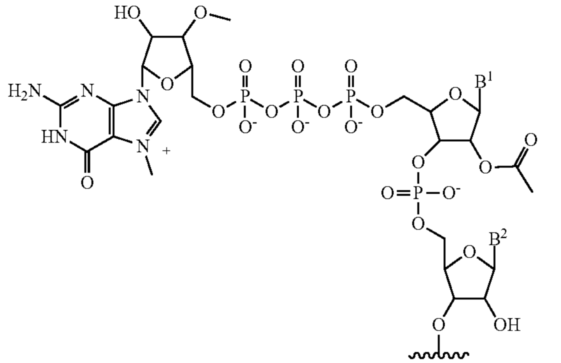

II-e

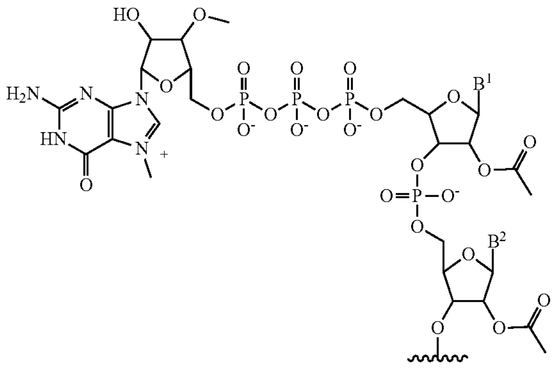

II-f

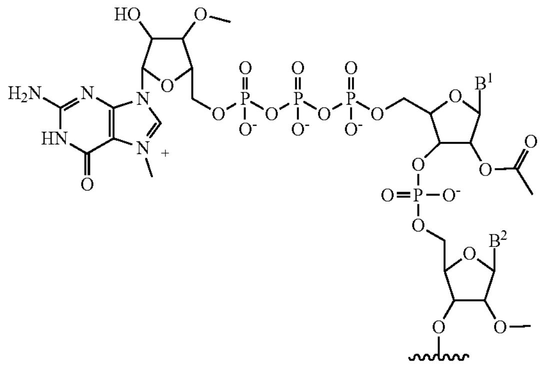

or a salt thereof.

Embodiment 29. The polyribonucleotide according to embodiment 27 or 28, wherein $B^1$ is a natural base.

Embodiment 30. The polyribonucleotide according to embodiment 31, wherein the natural base is adenine.

Embodiment 31. The polyribonucleotide according to embodiment 29, wherein the natural base is cytosine.

Embodiment 32. The polyribonucleotide according to embodiment 29, wherein the natural base is guanine.

Embodiment 33. The polyribonucleotide according to embodiment 29, wherein the natural base is uracil.

Embodiment 34. The polyribonucleotide according to embodiment 27 or 28, wherein $B^1$ is a modified base.

Embodiment 35. The polyribonucleotide according to embodiment 35, wherein the modified base is N1-methylpseudouracil, a pyridin-4-one, 5-aza-uracil, 6-aza-uracil, 2-thio-5-aza-uracil, 2-thio-uracil, 5-methyl cytosine, 5-aza-cytosine, 6-aza-cytosine, pseudoisocytosine, 3-methyl-cytosine, 5-formyl-cytosine, N4-methyl-cytosine, a 2-aminopurine, a 2,6-diaminopurine, a 2-amino-6-halo-purine, a 6-halo-purine, hypoxanthine, 1-methyl-hypoxanthine, 4,6-dimethyl-3,3a,4,9a-tetrahydro-9H-imidazo[1,2-a]purin-9-one, 4,6,7-trimethyl-3,3a,4,9a-tetrahydro-9H-imidazo[1,2-a]purin-9-one, N4-acetylcytosine, or 5-hydroxymethyluracil.

Embodiment 36. The polyribonucleotide according to embodiment 34, wherein the modified base is N1-methylpseudouracil.

Embodiment 37. The polyribonucleotide according to embodiment 34, wherein the modified base is N4-acetylcytosine.

Embodiment 38. The polyribonucleotide according to embodiment 34, wherein the modified base is 5-hydroxymethyluracil.

Embodiment 39. The polyribonucleotide according to any one of embodiments 27-38, wherein the natural base or modified base of $B^1$ further comprises a modified ribose.

Embodiment 40. The polyribonucleotide according to embodiment 39, wherein the modified ribose comprises a 2'-O acetyl group.

Embodiment 41. The polyribonucleotide according to embodiment 39 or 40, wherein $B^1$ is

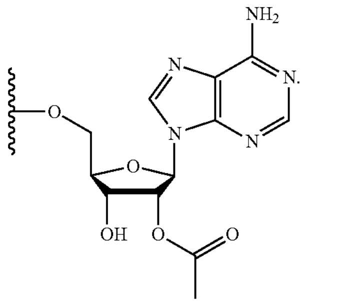

Embodiment 42. The polyribonucleotide according to embodiment 39 or 40, wherein $B^1$ is

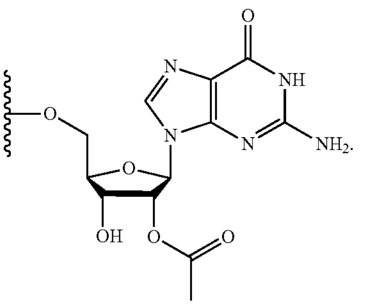

Embodiment 43. The polyribonucleotide according to embodiment 39 or 40, wherein $B^1$ is

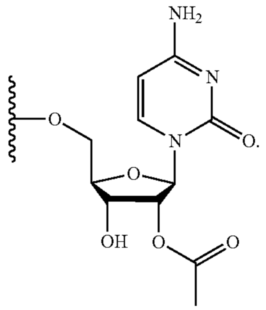

Embodiment 44. The polyribonucleotide according to embodiment 39 or 40, wherein $B^1$ is

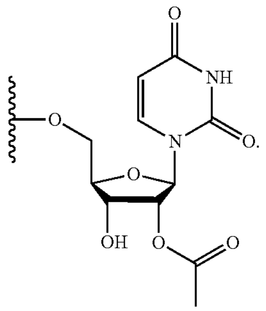

Embodiment 45. The polyribonucleotide according to embodiment 39 or 40, wherein $B^1$ is

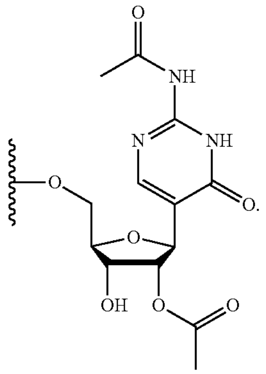

Embodiment 46. The polyribonucleotide according to embodiment 39 or 40, wherein $B^1$ is

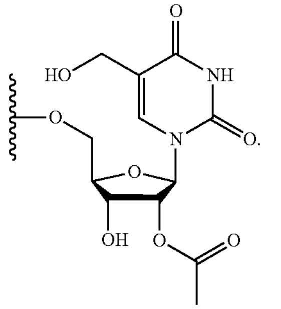

Embodiment 47. The polyribonucleotide according to embodiment 39 or 40, wherein $B^1$ is

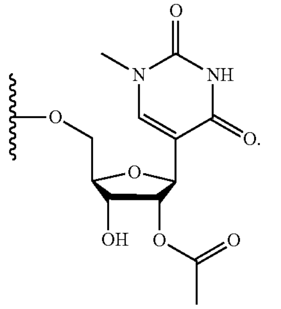

Embodiment 48. The polyribonucleotide of embodiment 27, wherein $R^1$ is hydrogen.

Embodiment 49. The polyribonucleotide of embodiment 27, wherein $R^1$ is $C_{1-6}$ alkyl.

Embodiment 50. The polyribonucleotide of embodiment 27, wherein $R^1$ is $—C(=O)CH_3$.

Embodiment 51. The polyribonucleotide of embodiment 27, wherein $R^2$ is hydrogen.

Embodiment 52. The polyribonucleotide of embodiment 27, wherein $R^2$ is $—CH_3$.

Embodiment 53. The polyribonucleotide of embodiment 27, wherein X is O.

Embodiment 54. The polyribonucleotide of embodiment 27, wherein X is S.

Embodiment 55. The polyribonucleotide of any one of embodiments 11-54, wherein the polyribonucleotide comprises a coding region sequence.

Embodiment 56. The polyribonucleotide of embodiment 55, wherein the coding region encodes a gene product.

Embodiment 57. The polyribonucleotide of embodiment 56, wherein the gene product is a payload.

Embodiment 58. The polyribonucleotide of embodiment 56 or 57, wherein the gene product is or comprises a polypeptide.

Embodiment 59. The polyribonucleotide of embodiment 56 or 57, wherein the gene product is or comprises a transcript.

Embodiment 60. The polyribonucleotide of embodiment 56 or 57, wherein the gene product is or comprises a messenger RNA (mRNA).

Embodiment 61. The polyribonucleotide of embodiment 56 or 57, wherein the gene product is or comprises a gRNA.

Embodiment 62. The polyribonucleotide of embodiment 56 or 57, wherein the gene product is or comprises an inhibitory RNA.

Embodiment 63. The polyribonucleotide of embodiment 56 or 57, wherein the gene product is or comprises an miRNA.

Embodiment 64. The polyribonucleotide of embodiment 56 or 57, wherein the gene product is or comprises an siRNA.

Embodiment 65. The polyribonucleotide of embodiment 56 or 57, wherein the gene product is or comprises an antisense oligonucleotide.

Embodiment 66. The polyribonucleotide of embodiment 56 or 57, wherein the gene product is or comprises a long non-coding RNA.

Embodiment 67. A composition comprising the polyribonucleotide of any one of embodiments 11-66.

Embodiment 68. The composition of embodiment 67, wherein the composition is a pharmaceutical composition.

Embodiment 69. The composition of embodiment 68, wherein the pharmaceutical composition is or comprises an immunogenic composition, a vaccine, a gene therapy, a chemotherapy, a protein replacement therapy, an immunotherapy, an antibody therapy, an immune-modulation therapy, a cell engineering therapy, or any combination thereof.

Embodiment 70. A cell comprising the polyribonucleotide of any one of embodiments 11-66.

Embodiment 71. A method comprising administering one or more polyribonucleotides according to any one of embodiments 11-66, or a composition according to any one of embodiments 67-69 to a cell, tissue or subject.

Embodiment 72. The method of embodiment 71, further comprising determining cell viability of the cell, tissue or subject, to which the polyribonucleotide or a composition comprising the same has been administered, wherein the cell, tissue or subject exhibits substantially the same cell viability as compared to a reference cell viability.

Embodiment 73. The method of embodiment 72, wherein the reference cell viability is the viability of a cell that has been administered a polyribonucleotide that does not include a compound having the Formula II or a salt thereof; or a composition comprising a polyribonucleotide that does not include a compound having the Formula II or a salt thereof.

Embodiment 74. The method of any one of embodiments 71-73, further comprising determining expression and/or activity of a payload.

Embodiment 75. The method of embodiment 74, wherein the payload is or comprises a polypeptide encoded by the polyribonucleotide.

Embodiment 76. The method of embodiment 74, wherein the payload is or comprises an RNA situated in the polyribonucleotide.

Embodiment 77. The method of any one of embodiments 74-76, wherein the cell, tissue or subject exhibits increased expression and/or activity of the payload as compared to expression and/or activity of the payload in a reference cell, tissue or subject.

Embodiment 78. The method of any one of embodiments 74-76, wherein the cell, tissue or subject exhibits substantially similar expression and/or activity of the payload as compared to expression and/or activity of the payload in a reference cell, tissue or subject.

Embodiment 79. The method of embodiment 77 or 78, wherein the reference cell, tissue or subject that has been administered: a polyribonucleotide that does not include a compound having the Formula II or a salt thereof; or a composition comprising a polyribonucleotide that does not include a compound having the Formula II or a salt thereof.

Embodiment 80. The method of any one of embodiments 74-79, wherein determining expression of the payload comprises determining expression of a polyribonucleotide, or a polypeptide, or both.

Embodiment 81. The method of any one of embodiments 71-80, wherein the method is: (i) a method to stimulate an immune response; (ii) an antibody therapy method; (iii) an immune-modulation method; (iv) a vaccination method; (v) a gene therapy method; (vi) a cell therapy engineering method; (vii) an immunotherapy method; (viii) a protein replacement therapy method; (ix) a chemotherapeutic method; or (x) any combination of (i)-(ix).

Embodiment 82. The method of any one of embodiments 71-81, wherein the cell is a mammalian cell, the tissue is a mammalian tissue, or the subject is a mammal.

Embodiment 83. The method of embodiment 82, wherein the subject is a human.

Embodiment 84. A composition comprising one or more polyribonucleotides according to any one of embodiments 11-66, or a composition according to any one of embodiments 67-69, for use in administering to a cell, tissue, or subject.

Embodiment 85. Use of a composition comprising one or more polyribonucleotides according to any one of embodiments 11-66, or a composition according to any one of embodiments 67-69, in the manufacture of a medicament for use in administering to a cell, tissue, or subject.

Embodiment 86. The composition for use of embodiment 84, or the use of embodiment 85, further comprising determining cell viability of the cell, tissue or subject, to which the polyribonucleotide or a composition comprising the same has been administered, wherein the cell, tissue or subject exhibits substantially the same cell viability as compared to a reference cell viability.

Embodiment 87. The composition for use of embodiment 84, or the use of embodiment 85, wherein the reference cell viability is the viability of a cell that has been administered a polyribonucleotide that does not include a compound having the Formula II or a salt thereof; or a composition comprising a polyribonucleotide that does not include a compound having the Formula II or a salt thereof.

Embodiment 88. The composition for use of embodiment 84, or the use of embodiment 85, further comprising determining expression and/or activity of a payload.

Embodiment 89. The composition for use, or the use of embodiment 88, wherein the payload is or comprises a polypeptide encoded by the polyribonucleotide.

Embodiment 90. The composition for use, or the use of embodiment 88, the payload is or comprises an RNA situated in the polyribonucleotide.

Embodiment 91. The composition for use, or the use of any one of embodiments 88-90, wherein the cell, tissue or subject exhibits increased expression and/or activity of the payload as compared to expression and/or activity of the payload in a reference cell, tissue or subject.

Embodiment 92. The composition for use, or the use of any one of embodiments 88-90, wherein the cell, tissue or subject exhibits substantially similar expression and/or activity of the payload as compared to expression and/or activity of the payload in a reference cell, tissue or subject.

Embodiment 93. The composition for use, or the use of any one of embodiments 88-90, wherein the reference cell, tissue or subject that has been administered: a polyribonucleotide that does not include a compound having the Formula II or a salt thereof; or a composition comprising a polyribonucleotide that does not include a compound having the Formula II or a salt thereof.

Embodiment 94. The composition for use, or the use of any one of embodiments 88-90, wherein determining expression of the payload comprises determining expression of a polyribonucleotide, or a polypeptide, or both.

Embodiment 95. The composition for use of any one of embodiments 84-94, or the use of any one of embodiments 85-94, wherein the use is for: (i) a method to stimulate an immune response; (ii) an antibody therapy method; (iii) an immune-modulation method; (iv) a vaccination method; (v) a gene therapy method; (vi) a cell therapy engineering method; (vii) an immunotherapy method; (viii) a protein replacement therapy method; (ix) a chemotherapeutic method; or (x) any combination of (i)-(ix).

Embodiment 96. The composition for use of any one of embodiments 84-94, or the use of any one of embodiments 85-94, wherein the cell is a mammalian cell, the tissue is a mammalian tissue, or the subject is a mammal.

Embodiment 97. The composition for use or the use of embodiment 96, wherein the subject is a human.

Embodiment 98. An in vitro transcription mixture comprising: (i) a DNA template; (ii) at least one RNA polymerase or a variant or a fragment thereof; (iii) a plurality of ribonucleotides; and (iv) a compound having the Formula II, or a salt thereof.

Embodiment 99. A method of making a polyribonucleotide, comprising a step of incubating an in vitro transcription mixture, wherein the in vitro transcription mixture comprises: (i) a DNA template; (ii) at least one RNA polymerase or a variant or a fragment thereof; (iii) a plurality of ribonucleotides; and (iv) a compound having the Formula II, or a salt thereof.

Embodiment 100. The method of embodiment 99, wherein the in vitro transcription mixture is incubated at a pH of about 5-8.

Embodiment 101. The method of embodiment 99, wherein the in vitro transcription mixture is incubated at a temperature of at least 37° C.

Embodiment 102. The method of embodiment 99, wherein the in vitro transcription mixture is incubated at a temperature of about 45° C. to about 55° C.

Embodiment 103. The method of any one of embodiments 99-102, wherein the method produces a plurality of polyribonucleotides.

Embodiment 104. The in vitro transcription mixture of embodiment 98 or the method of embodiment 99, wherein the plurality of ribonucleotides comprises one or more modified ribonucleotides comprising: a modified nucleobase, a modified ribose, a modified backbone, or any combination thereof.

Embodiment 105. The in vitro transcription mixture or the method of embodiment 104, wherein the one or more modified nucleobases comprise N1-methylpseudouracil, a pyridin-4-one, 5-aza-uracil, 6-aza-uracil, 2-thio-5-aza-uracil, 2-thio-uracil, 5-methyl cytosine, 5-aza-cytosine, 6-aza-cytosine, pseudoisocytosine, 3-methyl-cytosine, 5-formyl-cytosine, N4-methyl-cytosine, a 2-amino-purine, a 2,6-diaminopurine, a 2-amino-6-halo-purine, a 6-halo-purine, hypoxanthine, 1-methyl-hypoxanthine, 4,6-dimethyl-3,3a,4,9a-tetrahydro-9H-imidazo[1,2-a]purin-9-one, 4,6,7-trimethyl-3,3a,4,9a-tetrahydro-9H-imidazo[1,2-a]purin-9-one, N4-acetylcytosine, or 5-hydroxymethyluracil, or any combination thereof.

Embodiment 106. The in vitro transcription mixture or the method of embodiment 104 or 105, wherein the one or more modified nucleobases comprises a modified ribose.

Embodiment 107. The vitro transcription mixture or the method of embodiment 106, wherein the modified ribose comprises a 2'-O-acetylated ribose.

EXEMPLIFICATION

The invention now being generally described, will be more readily understood by reference to the following examples, which are included merely for purposes of illustration of some aspects and embodiments of the present invention, and is not intended to be limiting.

Example 1: Template DNA Production

The present example describes certain exemplary methods of in vitro synthesis of template polyribonucleotides that may be utilized in some embodiments of the present disclosure.

Polyribonucleotides of the present disclosure are not limited by the size nor structure of the protein-encoding sequences encoded by a payload sequence therein. Rather, polyribonucleotides of the present disclosure are suitable for the expression of any polypeptide, including large molecular weight proteins. Solely as an example, polyribonucleotides of the present disclosure were designed to encode an optimized version of firefly luciferase.

Template DNA Production: A Luc2 gene encoding an optimized version of firefly luciferase flanked by the *Xenopus* globin 5' and 3' UTRs was amplified from a cloned gene synthesis product (IDT). Amplification was carried out at an annealing temperature of 50° C. in a 20 μL reaction consisting of 0.25 μM each primer T7-AGG+6_fwd (SEQ ID NO: 1) and 120 pA_rev (SEQ ID NO: 2), 1× Herculase II buffer, 25 mM each dNTP, 15 ng plasmid, and 0.4 μL Herculase II enzyme. Reactions were treated with 20U Dpn1 (New England Biolabs) and purified into 30 uL nuclease free water by Zymo C&C25 spin column (Zymo Research).

The sequence of primers used were as follows:

```
T7-AGG + 6_fwd:
                                        (SEQ ID NO: 1)
gaattTAATA CGACTCACTA TAAGGaaaaaacttgt tctttttgca

gaagc

120pA_rev:
                                        (SEQ ID NO: 2)
TTTTTTTTTT TTTTTTTTTT TTTTTTTTTT TTTTTTTTTT

TTTTTTTTTT TTTTTTTTTT TTTTTTTTTT TTTTTTTTTT

TTTTTTTTTT TTTTTTTTTT TTTTTTTTTT TTTTTTTTTT

agaatgtgaa gaaactttct ttttattag
```

Example 2: In Vitro Transcription (IVT) of RNA Templates

The present example describes certain exemplary methods of in vitro transcription of polyribonucleotides that may be utilized in some embodiments of the present disclosure.

Methods: Luc2 RNA was synthesized in 20 μL IVT reactions consisting of 200 ng Luc2 T7 template, 20 mM MgCl2, 7.5 mM each of ATP, GTP, N4-acetylCTP, 5-hydroxymethylUTP, 7.5 mM cap reagent, 1× HiScribe Transcription Buffer, and 2 uL HiScribe polymerase mix (NEB) and incubated at 37° C. for 2 hours. Reactions were treated with 2U DNase I (NEB) and 20U CIAP (Promega) for 5 minutes at 37° C. to remove DNA template and residual low frequency 5' triphosphate ends. All IVT products were cleaned up using Monarch 500 μg RNA Clean Up kit (NEB) and eluted into nuclease-free water.

RNA quantification: RNA yield was determined using a NanoDrop OneC spectrophotometer.

Cell culture methods: Human Skeletal Myoblasts (ATCC) were cultured in DMEM (Thermo Fisher Scientific) supplemented with 2% Horse Serum (Thermo Fisher Scientific). They were thawed in a 37° C. water bath and suspended in 7 mL of the differentiation media. The cells were centrifuged at 180×g for 5 minutes, resuspended in 6 mL of differentiation media and centrifuged a final time at 180×g for 5 minutes. They were resuspended in 6 mL of differentiation media. Next, the concentration was measured and 4.8e4 cells from the diluted cell solution were added to the wells of cell culture-treated 96-well plates. Cells were incubated at 37° C. and at 5% CO2 for 72 hours. At 72 hours, the media was removed. The cells were washed with 200 μL of PBS and 200 μL of fresh differentiation media was added. The cells were transfected with 50 ng of each Luciferase reporter mRNA using MessengerMax Transfection Reagent (Thermo Fisher Scientific). After transfection, cells were incubated at 37° C. and 5% CO2 for 24 hours. Luciferase reporter expression and cell viability were measured at 24 hours post-transfection using the ONE-Glo+Tox Lucif and Cell Viability Assay (Promega) according to manufacturer's protocol.

Results: Table 1 shows the concentrations of respective RNA yields of Luc2 RNA capped with CleanCap® Reagent AG and Luc2 RNA capped with 2'-O-acetyl Cap. FIG. 1 shows the structure of the 2'-O-acetyl Cap used in this Example.

TABLE 1

RNA yields

| RNA | Concentration (ng/μL) |
|---|---|
| Luc2 RNA capped with CleanCap ® AG | 1911.2 |
| Luc2 RNA capped with 2'-O-acetyl Cap | 1609.8 |

The RNA yield data demonstrates that polyribonucleotides comprising a 2'-O-acetyl Cap disclosed herein can be produced at appreciable and relatively similar yields compared to polyribonucleotides comprising the widely used CleanCap® AG.

Figure 2:
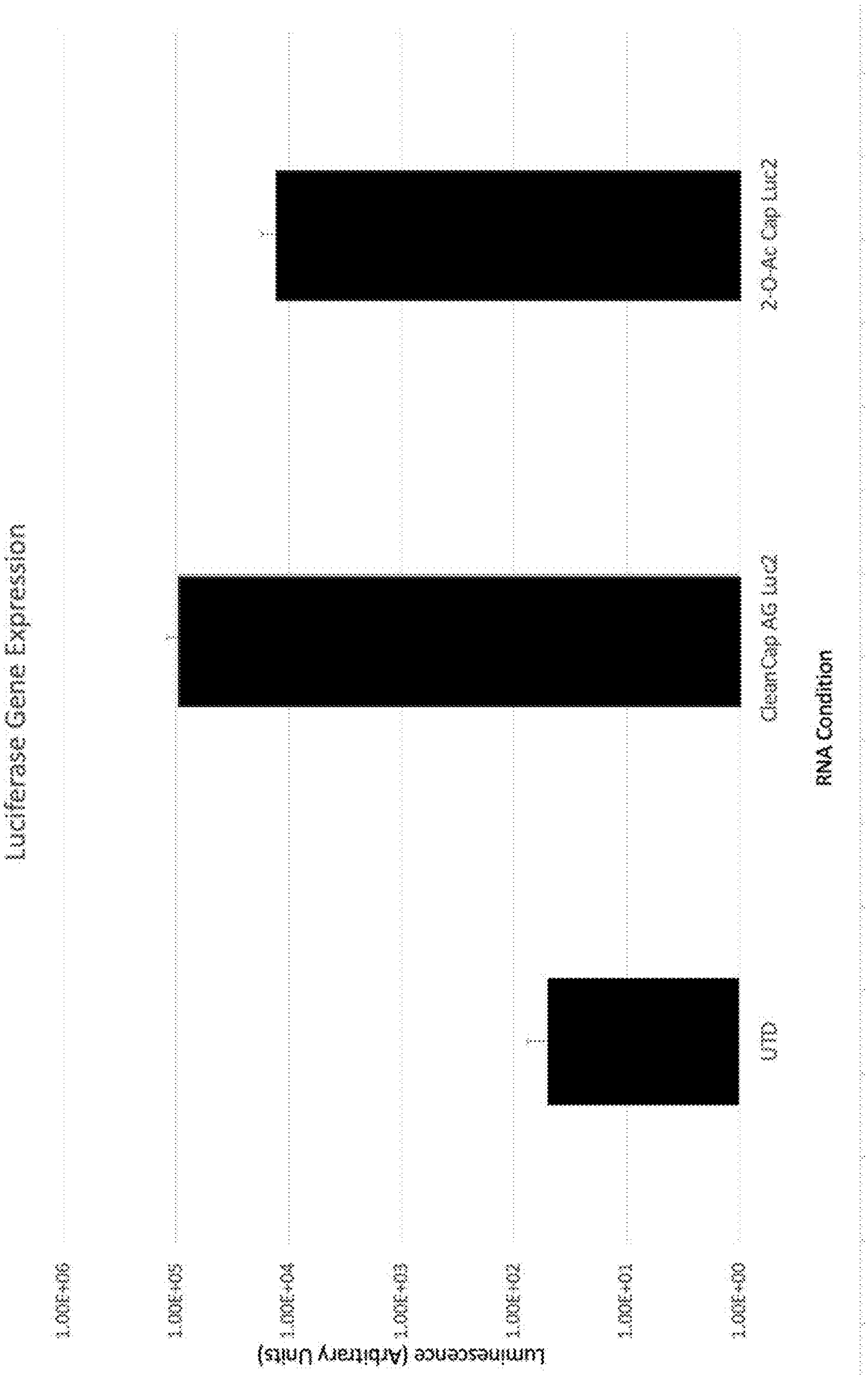
FIG. 2 is a graph of luciferase expression from human skeletal muscle cells from RNA synthesized with the indicated cap reagent.

As shown in FIG. 2, luciferase protein expression in hSKMC cells was comparable in cells transfected with Luc2 RNA capped with CleanCap® AG and in cells transfected with Luc2 RNA capped with a 2'-O-acetyl Cap. This data shows that polyribonucleotides comprising a 2'-O-acetyl Cap are functional and can be translated into polypeptides in vivo.

Figure 3:
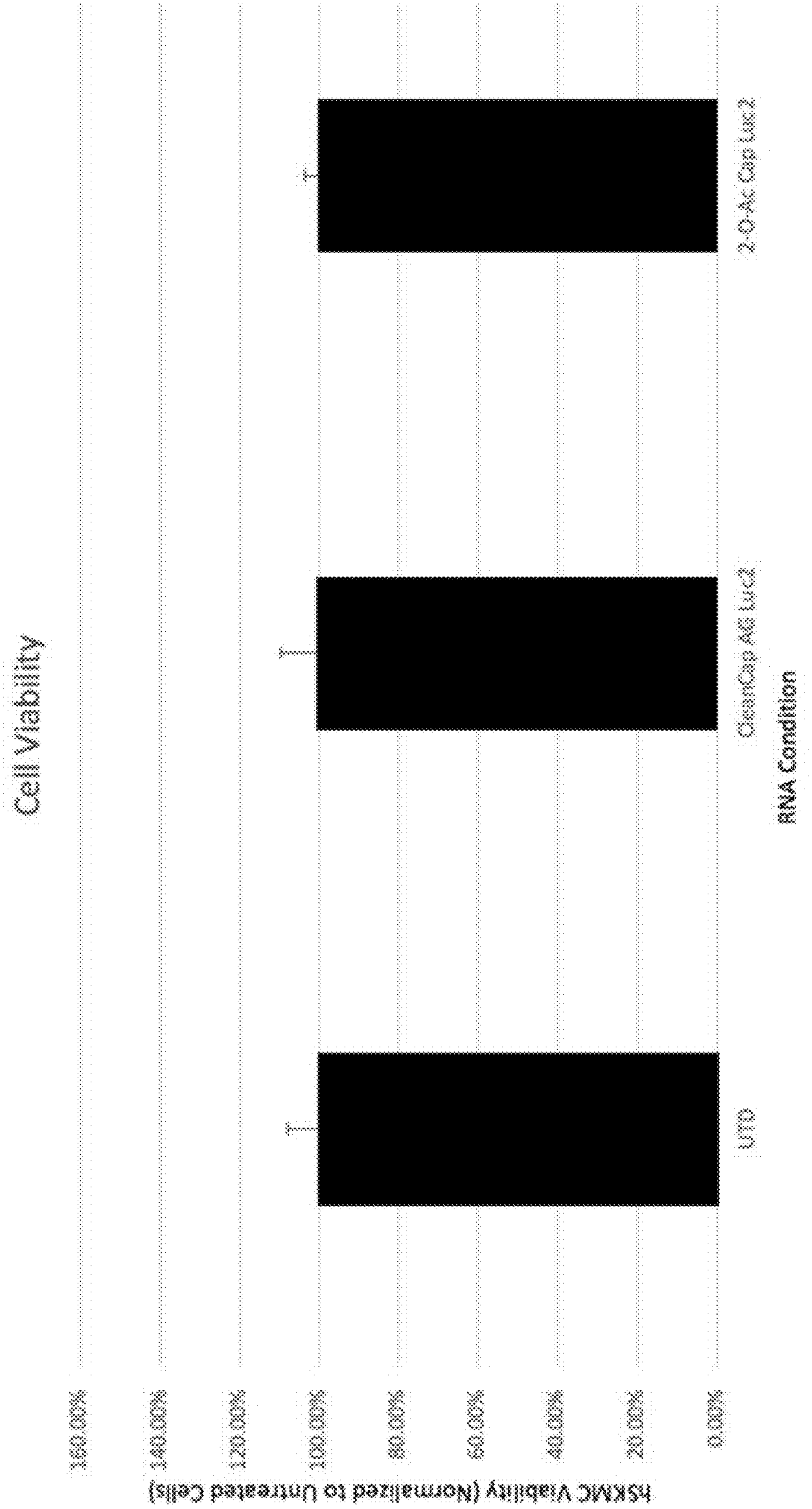
FIG. 3 shows a graph of viability of human skeletal muscle cells following transfection with respective RNA synthesized with the indicated cap reagent.

FIG. 3 shows that hSKMC cell viability was similar in cells transfected with Luc2 RNA capped with CleanCap® AG and in cells transfected with Luc2 RNA capped with a 2'-O-acetyl Cap. This data shows that polyribonucleotides comprising a 2'-O-acetyl Cap are well tolerated by cells.

Taken together the data shown herein demonstrates that the 2'-O-acetyl Cap disclosed herein performs similarly well to the commonly used CleanCap® AG reagent, and supports the development and use of polyribonucleotides comprising caps disclosed herein for various uses, including therapeutic uses.

EQUIVALENTS

Those skilled in the art will recognize, or be able to ascertain using no more than routine experimentation, many equivalents to the specific embodiments of the invention described herein. It is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Further, it should also be understood that any embodiment or aspect of the invention can be explicitly excluded from the claims, regardless of whether the specific exclusion is recited in the specification. The scope of the present invention is not intended to be limited to the above Description, but rather is as set forth in the claims that follow.

What is claimed is:

1. A compound of Formula I:

I

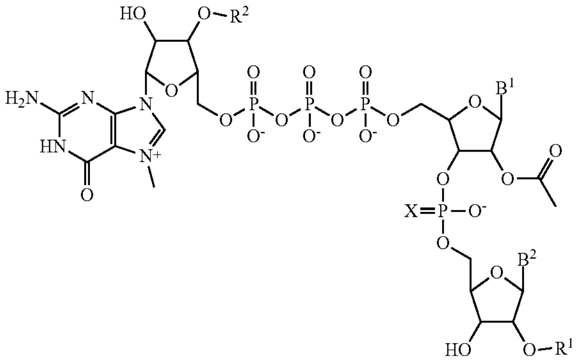

or a salt thereof, wherein:

each of $B^1$ and $B^2$ is independently selected from a natural base and a modified base;

$R^1$ is selected from hydrogen, $C_{1-6}$ alkyl, and —C(=O)$CH_3$;

$R^2$ is hydrogen or —$CH_3$; and

X is O or S.

2. The compound of claim 1, wherein the compound is selected from Formulae I-a, I-b, I-c, I-d, I-e, and I-f:

I-a

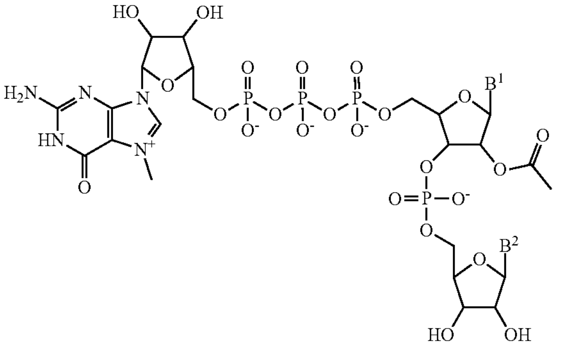

-continued

I-b

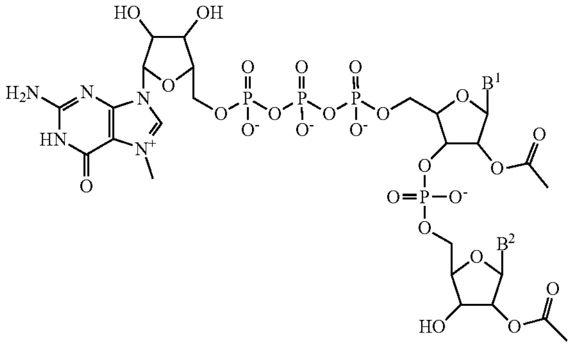

I-c

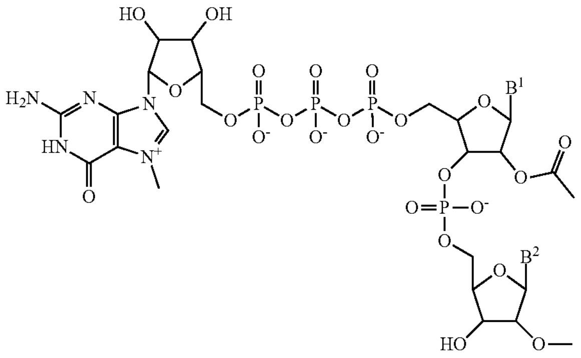

I-d

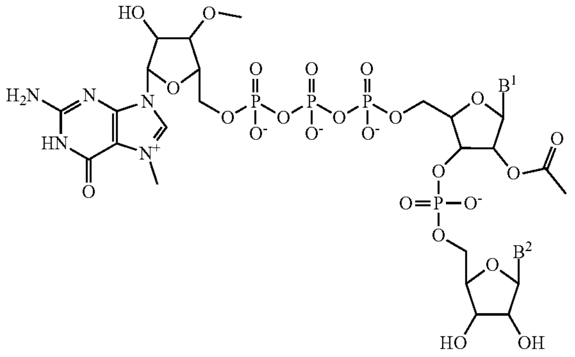

I-e

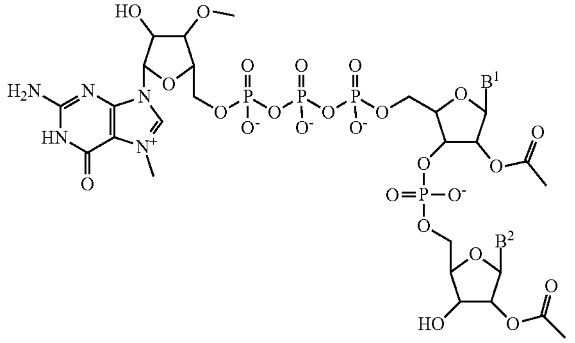

-continued

I-f

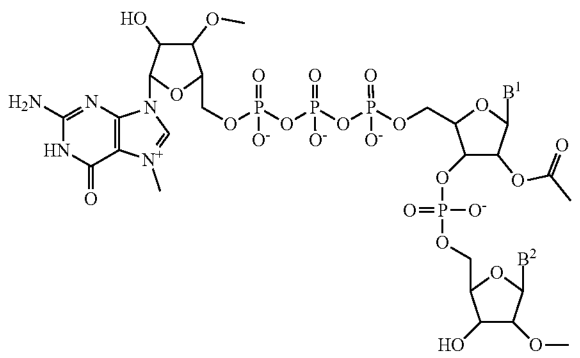

or a salt thereof.

3. The compound according to claim 1, wherein $R^1$ is hydrogen.

4. The compound according to claim 1, wherein $R^1$ is $C_{1-6}$ alkyl.

5. The compound according to claim 4, wherein $R^1$ is $—CH_3$.

6. The compound according to claim 1, wherein $R^1$ is $—C(═O)CH_3$.

7. The compound according to claim 1, wherein X is O.

8. The compound according to claim 1, wherein X is S.

9. The compound according to claim 1, wherein $B^1$ and/or $B^2$ is a modified base selected from N1-methylpseudouracil, a pyridin-4-one, 5-aza-uracil, 6-aza-uracil, 2-thio-5-aza-uracil, 2-thio-uracil, 5-methyl cytosine, 5-aza-cytosine, 6-aza-cytosine, pseudoisocytosine, 3-methyl-cytosine, 5-formyl-cytosine, N4-methyl-cytosine, a 2-amino-purine, a 2,6-diaminopurine, a 2-amino-6-halo-purine, a 6-halo-purine, hypoxanthine, 1-methyl-hypoxanthine, 4,6-dimethyl-3,3a,4,9a-tetrahydro-9H-imidazo[1,2-a]purin-9-one, 4,6,7-trimethyl-3,3a,4,9a-tetrahydro-9H-imidazo[1,2-a]purin-9-one, N4-acetylcytosine, and 5-hydroxymethyluracil.

10. The compound according to claim 1, wherein $B^1$ and/or $B^2$ is a natural base selected from guanine, adenine, cytosine, and uracil.

11. A polyribonucleotide comprising a compound having Formula II at the 5' end:

II

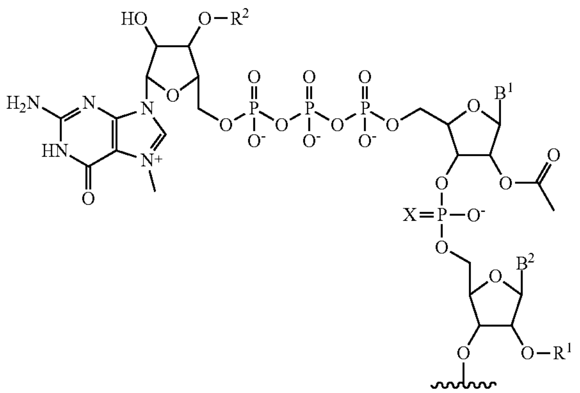

or a salt thereof, wherein:

~~~~ indicates the position at which the compound is attached to the polyribonucleotide;

each of $B^1$ and $B^2$ is independently selected from a natural base and a modified base;

$R^1$ is selected from hydrogen, $C_{1-6}$ alkyl, and $—C(═O)CH_3$;

$R^2$ is hydrogen or $—CH_3$; and

X is O or S.

12. The polyribonucleotide of claim 11, wherein the compound is selected from any of Formulae II-a, II-b, II-c, II-d, II-e, and II-f:

II-a

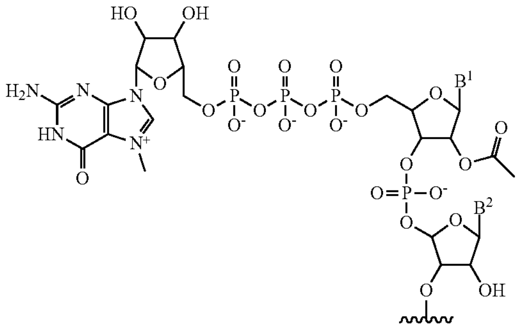

II-b

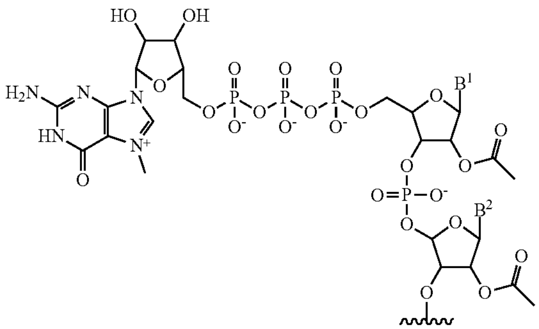

II-c

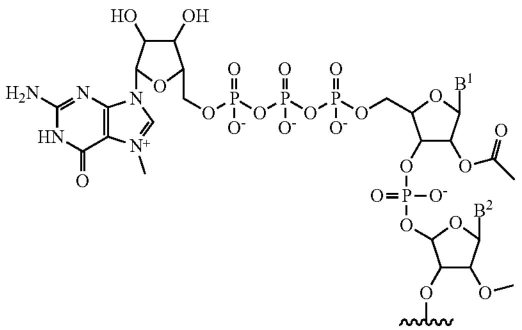

II-d

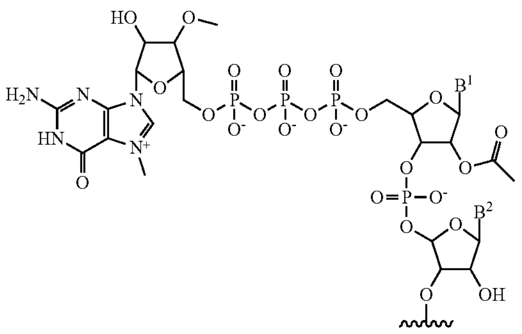
~~~~

-continued

II-e

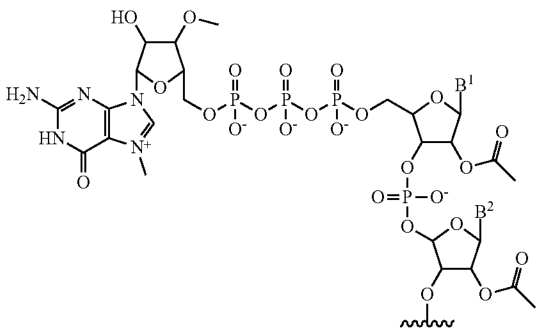

II-f

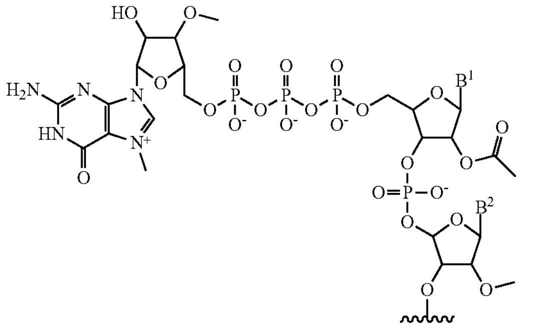

or a salt thereof.

13. The polyribonucleotide of claim 11, wherein $B^1$ and/or $B^2$ is a modified base selected from N1-methylpseudouracil, a pyridin-4-one, 5-aza-uracil, 6-aza-uracil, 2-thio-5-aza-uracil, 2-thio-uracil, 5-methyl cytosine, 5-aza-cytosine, 6-aza-cytosine, pseudoisocytosine, 3-methyl-cytosine, 5-formyl-cytosine, N4-methyl-cytosine, a 2-amino-purine, a 2,6-diaminopurine, a 2-amino-6-halo-purine, a 6-halo-purine, hypoxanthine, 1-methyl-hypoxanthine, 4,6-dimethyl-3,3a,4,9a-tetrahydro-9H-imidazo[1,2-a]purin-9-one, 4,6,7-trimethyl-3,3a,4,9a-tetrahydro-9H-imidazo[1,2-a]purin-9-one, N4-acetylcytosine, and 5-hydroxymethyluracil.

14. The polyribonucleotide of claim 11, wherein $B^1$ and/or $B^2$ is a natural base selected from guanine, adenine, cytosine, and uracil.

15. The polyribonucleotide of claim 11, wherein $B^1$ and/or $B^2$ comprises a modified ribose.

16. The polyribonucleotide of claim 15, wherein the modified ribose is a 2'O acetylated ribose.

17. The polyribonucleotide of claim 11, wherein the polyribonucleotide comprises a coding sequence encoding a payload.

18. The polyribonucleotide of claim 17, wherein the payload is or comprises a polypeptide.

19. The polyribonucleotide of claim 17, wherein the payload is or comprises an RNA.

20. A composition comprising the polyribonucleotide of claim 11.

21. The composition of claim 20, wherein the composition is a pharmaceutical composition, and wherein the pharmaceutical composition is or comprises an immunogenic composition, a vaccine, a gene therapy, a chemotherapy, a protein replacement therapy, an immunotherapy, an antibody therapy, an immune-modulation therapy, a cell engineering therapy, or any combination thereof.

22. An isolated cell comprising the polyribonucleotide of claim 11.

23. The compound of claim 10, wherein $B^1$ and/or $B^2$ is adenine.

24. The compound of claim 10, wherein $B^1$ and/or $B^2$ is guanine.

25. The compound of claim 10, wherein $B^1$ is adenine and $B^2$ is guanine.

26. The polyribonucleotide of claim 14, wherein $B^1$ and/or $B^2$ is adenine.

27. The polyribonucleotide of claim 14, wherein $B^1$ and/or $B^2$ is guanine.

28. The polyribonucleotide of claim 14, wherein $B^1$ is adenine and $B^2$ is guanine.

29. The composition of claim 20, wherein the composition is a pharmaceutical composition.

* * * * *